US008097711B2

(12) United States Patent
Timar et al.

(10) Patent No.: US 8,097,711 B2
(45) Date of Patent: Jan. 17, 2012

(54) THIOETHER SUBSTITUTED ARYL CARBONATE PROTECTING GROUPS

(75) Inventors: Zoltan Timar, Boulder, CO (US); Zoltan Kupihar, Szeged (HU); Douglas J. Dellinger, Boulder, CO (US); Marvin H. Caruthers, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 1172 days.

(21) Appl. No.: 11/897,898

(22) Filed: Aug. 31, 2007

(65) Prior Publication Data

US 2008/0146787 A1    Jun. 19, 2008

Related U.S. Application Data

(60) Provisional application No. 60/841,754, filed on Sep. 2, 2006.

(51) Int. Cl.
| | |
|---|---|
| *C12N 15/11* | (2006.01) |
| *A61K 48/00* | (2006.01) |
| *A61K 31/7042* | (2006.01) |
| *C07H 21/02* | (2006.01) |
| *C07H 21/04* | (2006.01) |
| *C07H 19/04* | (2006.01) |
| *C07H 19/048* | (2006.01) |
| *C07H 19/10* | (2006.01) |
| *C07H 19/20* | (2006.01) |

(52) U.S. Cl. .............. 536/23.1; 536/26.1; 536/26.7; 536/26.8; 514/44 R; 514/44 A; 514/47; 514/48; 514/51; 514/52

(58) Field of Classification Search .............. None
See application file for complete search history.

(56) References Cited

U.S. PATENT DOCUMENTS

| | | | | |
|---|---|---|---|---|
| 5,908,926 | A * | 6/1999 | Pirrung et al. | ............ 536/25.34 |
| 6,169,177 | B1 * | 1/2001 | Manoharan | ................ 536/25.31 |
| 6,222,030 | B1 | 4/2001 | Dellinger et al. | |
| 6,630,581 | B2 | 10/2003 | Dellinger et al. | |
| 7,067,641 | B2 | 6/2006 | Dellinger | |
| 7,101,986 | B2 | 9/2006 | Dellinger et al. | |
| 7,135,565 | B2 | 11/2006 | Dellinger et al. | |
| 7,193,077 | B2 | 3/2007 | Dellinger et al. | |
| 7,368,550 | B2 * | 5/2008 | Dellinger et al. | ............ 536/23.1 |
| 7,759,471 | B2 * | 7/2010 | Dellinger et al. | ............ 536/22.1 |
| 7,790,387 | B2 * | 9/2010 | Dellinger et al. | ................ 435/6 |
| 7,855,281 | B2 * | 12/2010 | Dellinger et al. | ............ 536/22.1 |
| 2005/0048496 | A1 | 3/2005 | Dellinger et al. | |
| 2005/0048497 | A1 | 3/2005 | Dellinger et al. | |
| 2005/0048601 | A1 | 3/2005 | Dellinger et al. | |
| 2005/0049407 | A1 | 3/2005 | Dellinger et al. | |
| 2006/0247430 | A1 | 11/2006 | Dellinger et al. | |
| 2006/0293511 | A1 | 12/2006 | Dellinger et al. | |
| 2007/0099859 | A1 | 5/2007 | Dellinger et al. | |
| 2007/0100136 | A1 | 5/2007 | Dellinger et al. | |
| 2007/0100137 | A1 | 5/2007 | Dellinger et al. | |
| 2007/0100138 | A1 | 5/2007 | Dellinger et al. | |

OTHER PUBLICATIONS

Agnieszka et al., "Solid-Phase Oligodeoxynucleotide Synthesis: A Two-Step Cycle Using Peroxy Anion Deprotection" Journal of the American Chemical Society (2003) vol. 125 pp. 13427-13441.*

* cited by examiner

*Primary Examiner* — Eric S Olson

(57) ABSTRACT

Embodiments of the invention include nucleotide and nucleoside monomers protected at the 5'- or 3'-hydroxyls with thioether substituted aryl carbonate protecting groups. In certain cases, the carbonate protecting groups include an aryl moiety, e.g., a phenyl group, attached to the carbonate, where the aryl moiety further includes a thioether group, e.g., an alkyl or aryl thioether group, bound directly to the aryl ring. Aspects of the invention further include methods of synthesizing nucleic acids, e.g., oligonucleotides, using such protected nucleoside monomer monomers, as well as nucleic acids produced using methods of the invention and compositions thereof.

12 Claims, 4 Drawing Sheets

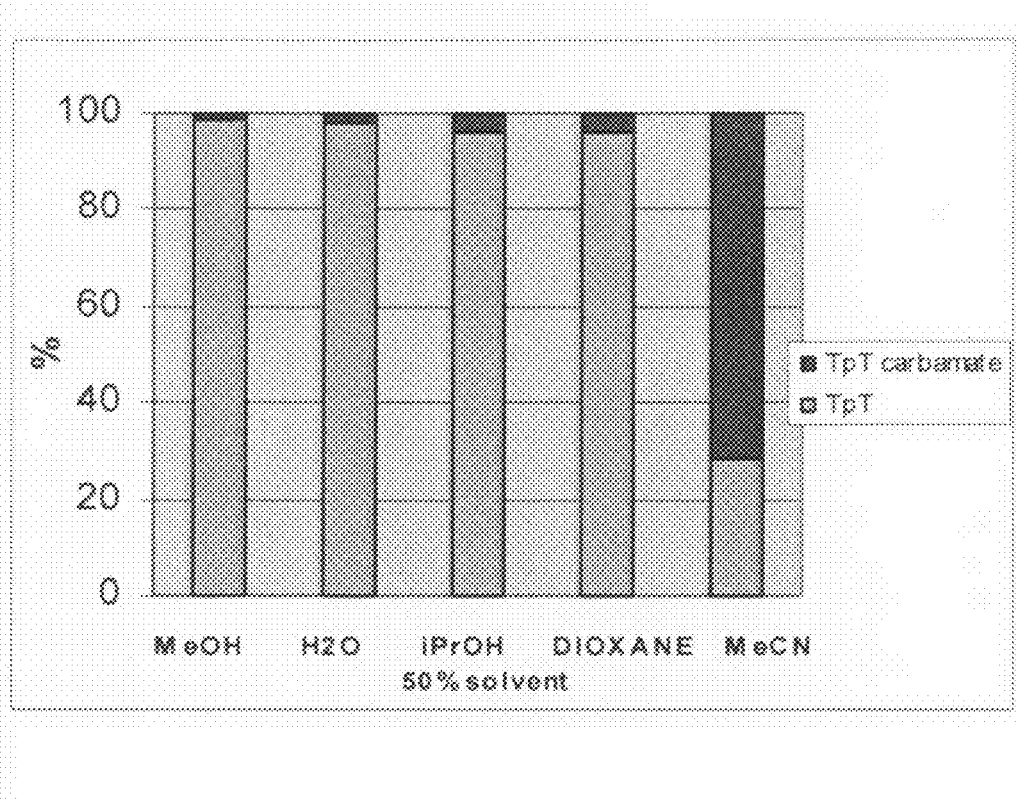

SEQUENCE LISTING

<160> NUMBER OF SEQ ID NOS: 4

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 1
atgtcaactc gtct                                                        14

<210> SEQ ID NO 2
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 2
atatatatat                                                             10

<210> SEQ ID NO 3
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 3

```
gtgtgtgtgt                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 4
ctctctctct                                                          10
```

THIOETHER SUBSTITUTED ARYL CARBONATE PROTECTING GROUPS

CROSS REFERENCE TO RELATED APPLICATIONS

This application claims the benefit under 35 U.S.C. §119 (e) of prior U.S. provisional application Ser. No. 60/841,754 filed Sep. 2, 2006, the disclosure of which is incorporated herein by reference.

INTRODUCTION

Solid phase chemical synthesis of DNA fragments is routinely performed using protected nucleoside phosphoramidites. Beaucage et al. (1981) Tetrahedron Lett. 22:1859. In this approach, the 3'-hydroxyl group of an initial 5'-protected nucleoside is first covalently attached to the polymer support. Pless et al. (1975) Nucleic Acids Res. 2:773. Synthesis of the oligonucleotide then proceeds by deprotection of the 5'-hydroxyl group of the attached nucleoside, followed by coupling of an incoming nucleoside-3'-phosphoramidite to the deprotected hydroxyl group. Matteucci et al. (1981) J. Am. Chem. Soc. 103:3185. The resulting phosphite triester is finally oxidized to a phosphotriester to complete one round of the synthesis cycle. Letsinger et al. (1976) J. Am. Chem. Soc. 98:3655. The steps of deprotection, coupling and oxidation are repeated until an oligonucleotide of the desired length and sequence is obtained. Optionally, after the coupling step, the product may be treated with a capping agent designed to esterify failure sequences and cleave phosphite reaction products on the heterocyclic bases.

The chemical group conventionally used for the protection of nucleoside 5'-hydroxyls is dimethoxytrityl ("DMT"), which is removable with acid. Khomma (1968) Pure Appl. Chem. 17:349; Smith et al. (1962) J. Am. Chem. Soc. 84:430. This acid-labile protecting group provides a number of advantages for working with both nucleosides and oligonucleotides. For example, the DMT group can be introduced onto a nucleoside regioselectively and in high yield. Brown et al. (1979) Methods in Enzymol. 68:109. Also, the lipophilicity of the DMT group greatly increases the solubility of nucleosides in organic solvents, and the carbocation resulting from acidic deprotection gives a strong chromophore, which can be used to indirectly monitor coupling efficiency. Matteucci et al. (1980) Tetrahedron Lett. 21:719. In addition, the hydrophobicity of the group can be used to aid separation on reverse-phase HPLC. Becker et al. (1985) J. Chromatogr. 326:219. While the phosphoramidite and phosphite triester approaches are most broadly used, but other approaches include the phosphodiester approach, the phosphotriester approach and the H-phosphonate approach.

SUMMARY

Embodiments of the invention include protected nucleoside monomers having carbonate protecting groups with a aryl moiety attached to a carbonate, wherein the aryl moiety comprises a thioether group bound to a aryl ring, i.e., thioether substituted aryl carbonate protecting groups.

Aspects of the invention include materials and methods for use in site-specific step-wise synthesis that yield polymer chains, e.g., as in the formation of nucleic acids, e.g., oligonucleotides. In certain embodiments, the synthesis protocol begins with the preparation of a first chain including at least one monomer. This preparation step includes, in certain embodiments, attaching the substituted monomer to an insoluble support. The substituted monomer is then deprotected if necessary to expose a reactive site. A second protected monomer having one or more hydroxyl protecting groups is reacted with the deprotected reactive site of the chain to yield an elongated chain.

In certain embodiments, a capping step may be included in the synthesis cycle, if desired. The elongated chain is then subjected to a combined oxidation/deprotection step which allows the oxidation and deprotection reactions to occur concurrently in the same reaction solution. That is, the oxidation of the backbone of the elongated chain, the oxidation of the thioether group on the carbonate protecting group, and the deprotection of the reactive site in the elongated chain occur at substantially the same time upon application of a single combined oxidation/deprotection reagent composition to the elongated chain. The deprotection of the reactive site on the elongated chain allows the cycle to repeat with the addition of the third substituted monomer. The synthesis cycle disclosed above is repeated until the desired chain length is achieved.

Embodiments of the methods provide for concurrent oxidation of the internucleoside linkage, oxidation of the thioether group on the carbonate protecting group, and removal of the hydroxyl protecting group, eliminating a step present in certain conventional processes for synthesizing oligonucleotides. In addition, the method can be used in connection with fluorescent or other readily detectable protecting groups, enabling monitoring of individual reaction steps. Further, the method is useful in carrying out either 3'-to-5' synthesis or 5'-to-3' synthesis. Embodiments of the methods are readily employed in highly parallel, microscale synthesis of oligonucleotides, e.g., in synthesis of nucleic acid arrays.

BRIEF DESCRIPTION OF THE FIGURES

FIG. 3. Efficiency of cleavage of 4-(methylthio)aryl carbonate protecting group by different 50% organic solvent—aqueous $H_2O_2$ mixtures

DEFINITIONS

Figure 1:
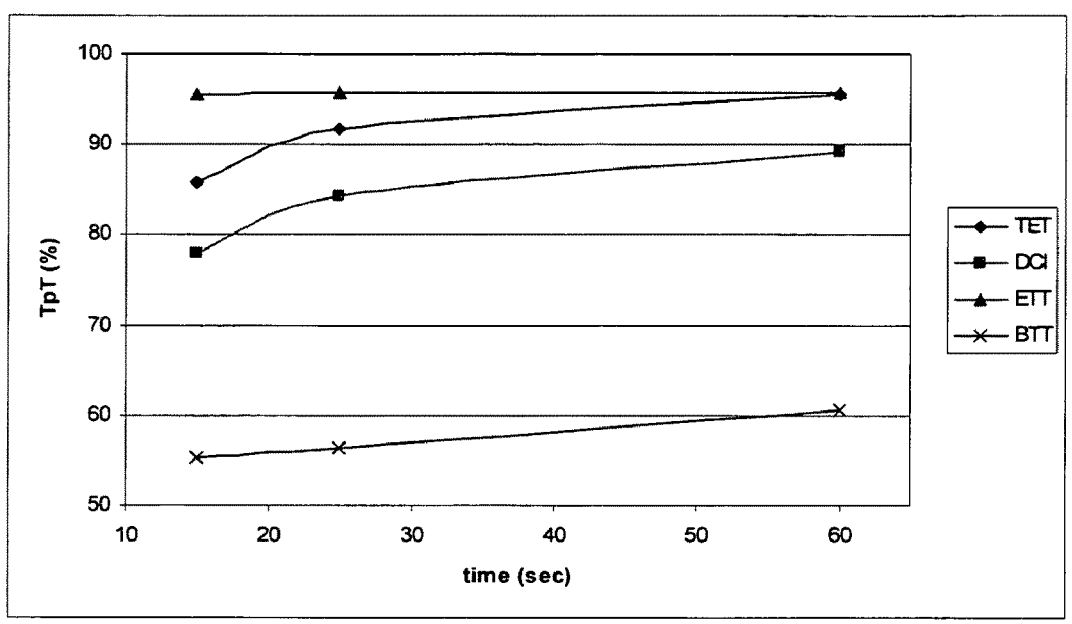
FIG. 1. Coupling yields in case of different activators
Figure 2A:
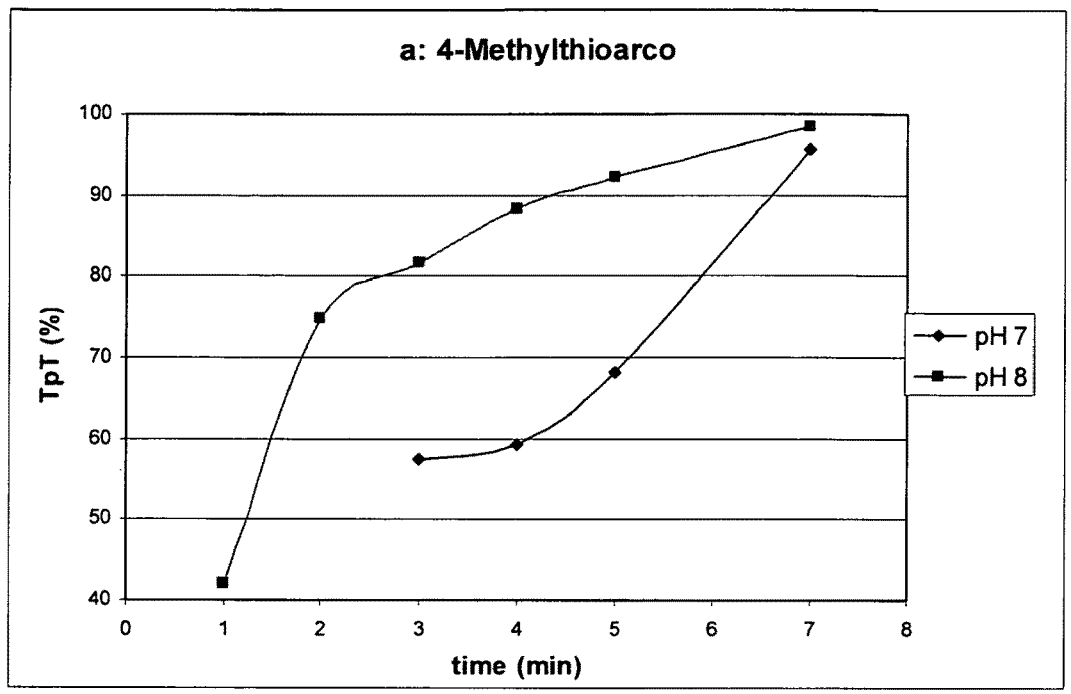
FIGS. 2A to 2D. Four different thioether substituted aryl carbonate protected TpTs on CPG were treated with pH 7 or 8 aq. $H_2O_2$ (6%) and then with aq. cc. $NH_4OH$. Two products are formed, TpT and $H_2NCOO$-TpT, the calculated deprotection yields (as TpT %) are plotted.
Figure 2B:
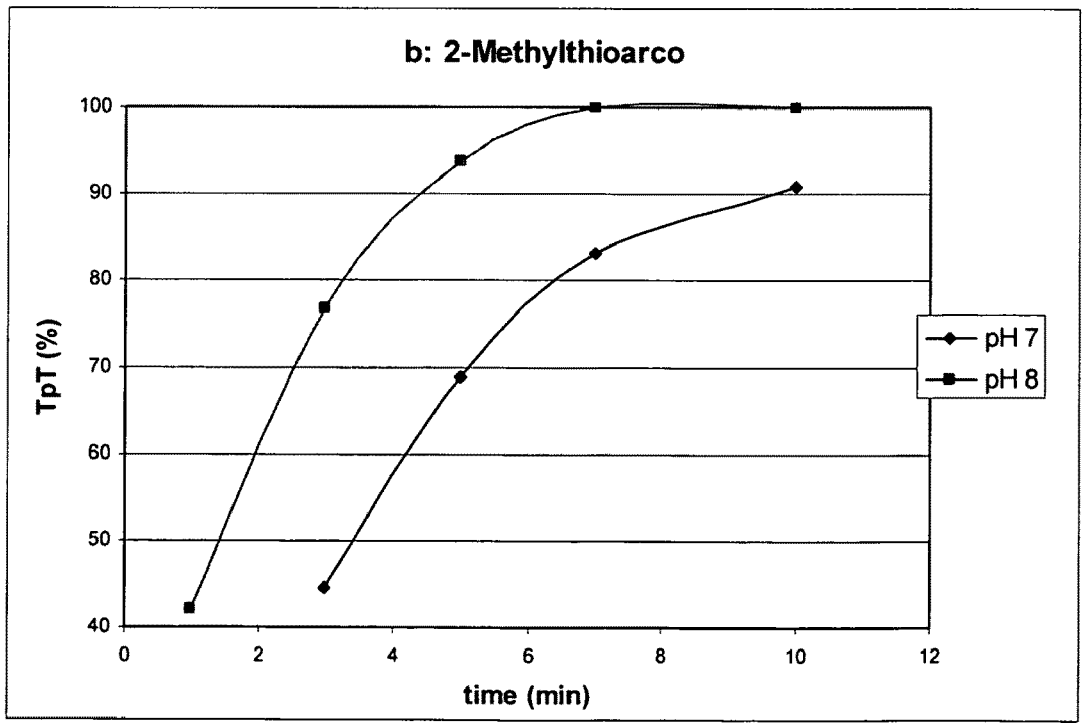
Figure 2C:
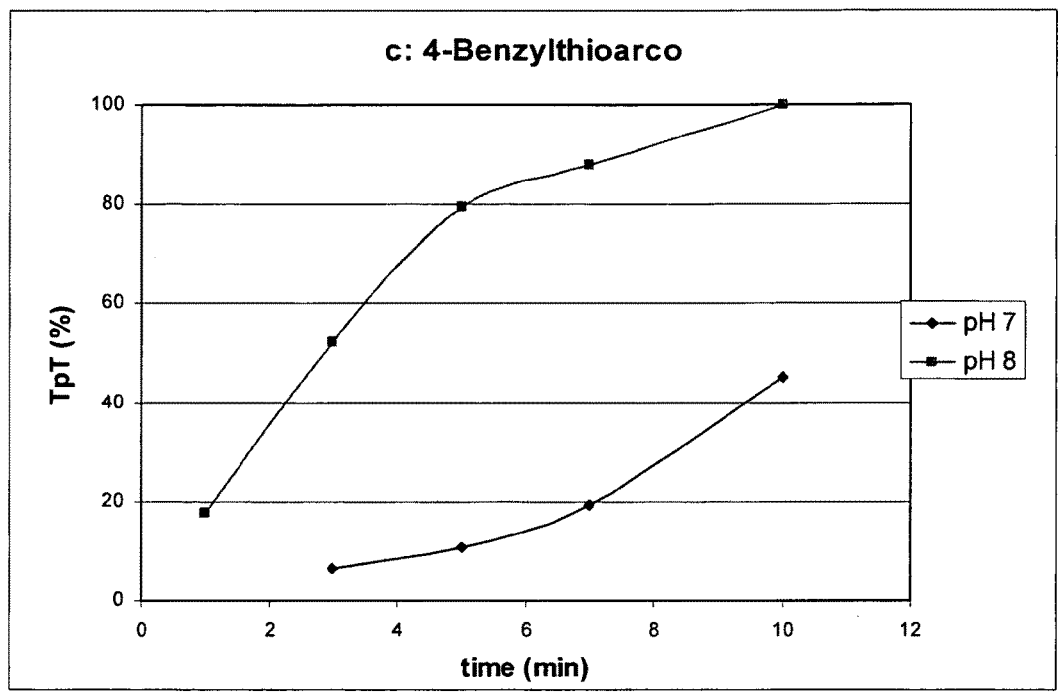
Figure 2D:
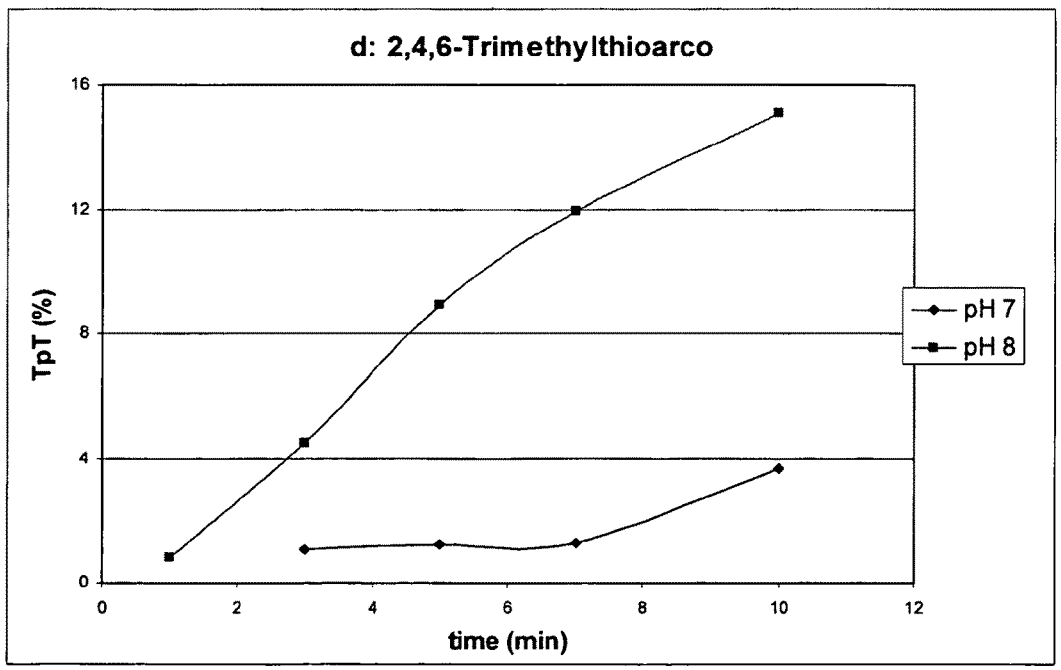

In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleobase" references the heterocyclic base of a nucleoside or nucleotide. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected.

As used herein, polynucleotides include single or multiple stranded configurations, where one or more of the strands may or may not be completely aligned with another. The terms "polynucleotide" and "oligonucleotide" are generic to polydeoxynucleotides (containing 2-deoxy-D-ribose), to polyribonucleotides (containing D-ribose), to any other type of polynucleotide having nucleotide subunits that are N-glycosides of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 200 nucleotides in length, while a "polynucleotide" includes a nucleotide multimer having at least two nucleotides and up to several thousand (e.g. 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "alkyl" as used herein, unless otherwise specified, refers to a saturated straight chain, branched or cyclic hydrocarbon group, which may vary in terms of carbon atoms, ranging in certain embodiments from 1 to 24 carbon atoms, such as 1-12 carbon atoms, where alkyl may be methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl moiety having additional groups, such as one or more linkages, e.g., selected from ether-, thio-, amino-, phospho-, oxo-, ester-, and amido-, and/or being substituted with one or more additional groups including, but not limited to, lower alkyl, aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to eight carbon atoms and further having additional groups, such as one or more linkages, e.g., selected from ether-, thio-, amino-, phospho-, keto-, ester- and amido-, and/or being substituted with one or more groups including lower alkyl, aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. In any given embodiments, the substituents from the above list that are chosen are ones that are compatible with the overall reaction scheme being employed, e.g., ones that do not cause unacceptable side reactions, etc. As such, in a given embodiments, any of the above groups are appropriate so long as they do not result in unacceptable side reactions.

"Hydrocarbyl" groups are univalent groups formed by removing a hydrogen atom from a hydrocarbon, e.g., ethyl phenyl. Substituted "hydrocarbyl" groups are hydrocarbyls that include one or more substituents, e.g., as defined above.

The term "alkoxy" as used herein refers to a substituent —O—R, wherein R is alkyl or modified alkyl as defined above. The term "lower alkoxy" refers to such a group wherein R is lower alkyl. The term "thioalkyl" as used herein refers to a substituent —S—R wherein R is alkyl or modified alkyl as defined above.

The term "alkenyl" as used herein, unless otherwise specified, refers to a branched, unbranched or cyclic (e.g. in the case of C5 and C6) hydrocarbon group, e.g., of 2 to 24, such as 2 to 12, carbon atoms containing at least one double bond, such as ethenyl, vinyl, allyl, octenyl, decenyl, and the like. The term "lower alkenyl" intends an alkenyl group of two to eight carbon atoms, and includes vinyl and allyl. The term "cycloalkenyl" refers to cyclic alkenyl groups.

The term "aryl" as used herein, unless otherwise specified, refers to a branched, or unbranched hydrocarbon group, e.g., of 2 to 24, such as 2 to 12, carbon atoms, containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing. 1 to 5 aromatic rings, either fused or linked, and either unsubstituted or substituted with 1 or more additional groups typically selected from lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl. Aryl groups of interest contain 1 to 3 fused aromatic rings, such as 1 aromatic ring or 2 fused aromatic rings. Aromatic groups herein may or may not be heterocyclic. The term "aralkyl" intends a moiety containing both alkyl and aryl species, e.g., containing about 24 carbon atoms or less, such about 12 carbon atoms or less in the alkyl segment of the moiety, and contain in certain embodiments 1 to 5 aromatic rings. The term "aralkyl" is used to refer to aryl-substituted alkyl groups. The term "aralkylene" is used in a similar manner to refer to moieties containing both alkylene and aryl species, such as about 24 or less carbon atoms in the alkylene portion and 1 to 5 aromatic rings in the aryl portion, and including aryl-substituted alkylene. Certain aralkyl groups have the structure —(CH$_2$)j-Ar wherein j is an integer in the range of 1 to 24, such as 1 to 6, and Ar is a monocyclic aryl moiety.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

The term "halo" or "halogen" is used in its conventional sense to refer to a chloro, bromo, fluoro or iodo substituent.

A "phospho" group includes phosphodiester, phosphotriester, and H-phosphonate groups. In the case of either a phospho or phosphite group, a chemical moiety other than a substituted 5-membered furyl ring may be attached to 0 of the phospho or phosphite group which links between the furyl ring and the P atom.

An "internucleotide bond" (or "internucleotide linkage") refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g. a sulfur atom or the nitrogen atom of a mono- or di-alkyl amino group.

The term "protecting group" as used herein refers to a species which prevents a portion of a molecule from undergoing a specific chemical reaction, but which is removable from the molecule following completion of that reaction, as taught for example in Greene, et al., "Protective Groups in Organic Synthesis," John Wiley and Sons, Second Edition, 1991. The "protected group" is the group that is protected by being bound to the protecting group. A "thioether substituted aryl carbonate protecting group" is a protecting group that includes a thioether substituted aryl carbonate group, wherein the carbonate group is the site at which the protecting group is bound to the group being protected (i.e. the protected group, e.g., the terminal 3'-OH or terminal 5'-OH of a polynucleotide intermediate during synthesis of a polynucleotide, or a 3'-OH or 5'-OH of a nucleoside phosphoramidite used in the synthesis of a polynucleotide). A "hydroxyl protecting group" refers to a protecting group where the protected group is a hydroxyl. "Reactive site hydroxyl" references a hydroxyl group capable of reacting with a precursor to result in an internucleotide bond being formed. In typical embodiments, the reactive site hydroxyl is the terminal 5'-hydroxyl during 3'-5' polynucleotide synthesis and is the terminal 3'-hydroxyl during 5'-3' polynucleotide synthesis.

As used herein, "cleaving", "cleavage", "deprotecting", "releasing", or like terms when used in reference to a protecting group refers to breaking a bond via which the protecting group is bound to the protected group, resulting in the cleaved protecting group and the deprotected moiety (the moiety that was the protected group when bound to the protecting group), where the cleaved protecting group is separate from the deprotected moiety.

As used herein, "concurrent" or "concurrently" is used to describe two or more different reactions that occur at substantially the same time under a given set of reaction conditions, e.g. in the same reaction vessel. For example, in particular embodiments described herein, concurrent reactions that may occur include deprotection of a hydroxyl group (e.g. of a polynucleotide intermediate), oxidation of a phosphate group (e.g. of the same polynucleotide intermediate), and oxidation of a thioether group (e.g. of the same polynucleotide intermediate). In this regard, "at substantially the same time" means the reactions occur within a few minutes of each other, e.g. within about 10 minutes, such as within about 2 minutes, including within about 30 seconds. Specifically contemplated are embodiments in which one of the concurrent reactions potentiates another of the concurrent reactions such that the first reaction occurs and then the second reaction takes place shortly thereafter, wherein the first and second reactions take place concurrently under a given set of reaction conditions, e.g. without any intervening addition of reagents or substantial change of temperature, pressure, or other component of the reaction mixture, or without any intervening separation or purification or other workup procedure or the like.

The term "electron withdrawing" denotes the tendency of a substituent to attract valence electrons of the molecule of which it is a part, i.e., an electron-withdrawing substituent is electronegative with respect to neighboring atoms. A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloro, and the like.

The term "electron-donating" refers to the tendency of a substituent to repel valence electrons from neighboring atoms, i.e., the substituent is less electronegative with respect to neighboring atoms. Exemplary electron-donating groups include amino, methoxy, alkyl (including alkyl having a linear or branched structure, alkyl having one to eight carbons), cycloalkyl (including cycloalkyl having four to nine carbons), and the like.

The term "alpha effect," as in an "alpha effect nucleophile" in a deprotection/oxidation agent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm. 171; Buncel et al. (1982) J. Am. Chem. Soc. 104:4896; Edwards et al. (1962) J. Am. Chem. Soc. 84:16; Evanseck et al. (1987) J. Am. Chem. Soc. 109:2349. The magnitude of the alpha effect is dependent upon the electrophile which is paired with the specific nucleophile. Mclsaac, Jr. et al. (1972), J. Org. Chem. 37:1037. Peroxy anions are example of nucleophiles which exhibit strong alpha effects.

"Moiety" and "group" are used interchangeably herein to refer to a portion of a molecule, typically having a particular functional or structural feature, e.g. a linking group (a portion of a molecule connecting two other portions of the molecule), or an ethyl moiety (a portion of a molecule with a structure closely related to ethane).

"Linage" as used herein refers to a first moiety bonded to two other moieties, wherein the two other moieties are linked via the first moiety. Linkages of interest include ether (—O—), oxo (—C(O)—), amino (—NH—), amido (—N—C(O)—), thio (—S—), phosphate (—PO$_4$H—), ester (C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Substituents of interest include nonhydrogen atoms (e.g. halogens), functional groups (such as, but not limited to, amino, sulfhydryl, carbonyl, hydroxyl, alkoxy, carboxyl, silyl, silyloxy, phosphate and the like), alkyl groups, and alkyl groups substituted with one or more heteroatoms. Accordingly, substituents of interest include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, amino, imino, amido, alkylamino, arylamino, alkoxy, aryloxy, thio, alkylthio, arylthio, alkyl; aryl, thioalkyl, hydroxyl, mercapto, halo, cyano, nitro, nitroso, azido, carboxy, sulfide, sulfonyl, sulfoxy, phosphoryl, silyl, silyloxy, and boronyl optionally substituted on one or more available carbon atoms with a nonhydrocarbyl substituent such as cyano, nitro, halogen, hydroxyl, sulfonic acid, sulfate, phosphonic acid, phosphate, or phosphonate or the like. Any substituents are typically chosen so as not to substantially adversely affect reaction yield (for example, not lower it by more than 20% (or 10%, or 5% or 1%) of the yield otherwise obtained without a particular substituent or substituent combination).

As used herein, "dissociation constant", e.g. an acid dissociation constant, has its conventional definition as used in the chemical arts and references a characteristic property of a molecule having a tendency to lose a hydrogen ion. The value of a dissociation constant mentioned herein is typically expressed as a negative $\log_{10}$ value, i.e. a pKa (for an acid dissociation constant).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

DETAILED DESCRIPTION

Embodiments of the invention include thioether substituted aryl carbonate protecting groups, and nucleoside monomers protected with thioether substituted aryl carbonate protecting groups. Aspects of the invention further included methods of synthesizing nucleic acids, e.g., oligonucleotides, using such protected nucleoside monomer monomers, as well as nucleic acids produced using methods of the invention and compositions thereof.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similiar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In a first embodiment, the invention pertains to a method for synthesizing a nucleic acid, e.g., an oligonucleotide, on a solid support, wherein a thioether substituted aryl carbonate protecting group is used as a protecting group for moiety on a nucleoside monomer, e.g., is used as a hydroxyl protecting group. Embodiments of the methods include a two-step cycle of (1) coupling a hydroxyl-protected nucleoside monomer to a growing oligonucleotide chain, and (2) applying a reagent solution that concurrently oxidizes the internucleoside linkage, oxidizes a thioether group on the carbonate protecting group, and removes the carbonate protecting group. The two-step cycle of coupling and deprotection/oxidation steps are repeated as necessary to give an oligonucleotide having a desired sequence and length.

In the initial step of the synthesis, an initial nucleoside is covalently attached to a solid support to serve as the starting point for oligonucleotide synthesis. The initial nucleoside may be bound to the support through its 3'-hydroxyl group or its 5'-hydroxyl group, and in certain embodiments is bound through the 3'-hydroxyl group. A second nucleoside monomer is then coupled to the free hydroxyl group of the support-bound initial nucleoside, wherein for 3'-to-5' oligonucleotide synthesis, the second nucleoside monomer has a phosphorus derivative such as a phosphoramidite at the 3' position and a thioether substituted aryl carbonate protecting group at the 5' position. Alternatively, for 5'-to-3' oligonucleotide synthesis, the second nucleoside monomer has a phosphorus derivative at the 5' position and a thioether substituted aryl carbonate protecting group at the 3' position. This coupling reaction gives rise to a newly formed internucleoside linkage between the initial nucleoside and the added nucleoside monomer, with the hydroxyl protecting group intact. In the second step of the synthesis, the thioether substituted aryl carbonate protecting group is removed with a combined oxidation/deprotection reagent solution that also serves to oxidize the phosphite group of the internucleoside linkage to result in the desired phospho group, e.g. to form a phosphodiester or phosphotriester internucleoside linkage.

In certain embodiments, for 3'-to-5' synthesis, a support-bound nucleoside monomer is provided having the structure (I)

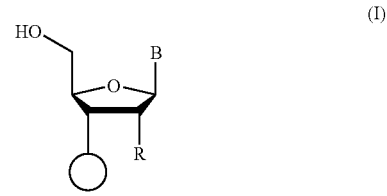

wherein:

represents the solid support or a support-bound oligonucleotide chain;

R is hydrido, hydroxy protecting group, fluoro, an alkoxy, O-ethyleneoxyalkyl (O—CH$_2$CH$_2$OR), a protected amino, a protected amido, or protected alkylamino wherein when R is hydrido, the support-bound nucleoside is a deoxyribonucleoside, as will be present in DNA synthesis, and when R is hydroxy protecting group), the support-bound nucleoside is a ribonucleoside, as will be present in RNA synthesis; and B is a heterocyclic base or a protected heterocyclic base, e.g. a purine or pyrimidine base.

In particular embodiments, the heterocyclic base may be a conventional purine or pyrimidine base, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, or the like. The purine or pyrimidine base may also be an analog of the foregoing; suitable analogs include, but are not limited to: 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

As reviewed above, employed in the subject methods are nucleoside monomers protected with a thioether substituted aryl carbonated protecting group. The protected monomer to be added has the structure of formula (II)

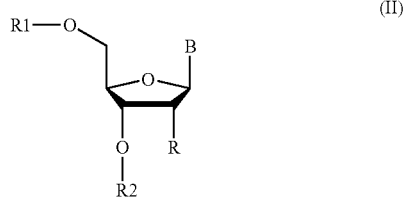

(II)

in which B and R are as defined above with respect to the support-bound nucleoside of structural formula (I) and R1 is a thioether substituted aryl carbonate protecting group as described herein.

In certain embodiments, the group R1 has the structure (III):

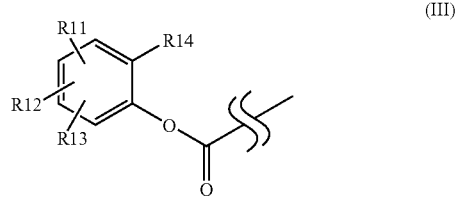

(III)

wherein:
the broken line denotes the site of attachment to the rest of structure (II) (e.g. to the 5'-carbon of the protected monomer);
R11 is a thioether moiety having the structure R15-S (wherein the S is bound directly to a ring carbon of structure (III) such that R15 is attached to the phenyl ring of structure (III) via a thio linkage);

R12 is selected from hydrido-, a thioether moiety having the structure R16-S (wherein the S is bound directly to a ring carbon of structure (III) such that R16 is attached to the phenyl ring of structure (III) via a thio linkage), or an electron-withdrawing substituent (such as nitro, acyl, formyl, sulfonyl, trifluoromethyl, cyano, chloro, and the like);

R13 is selected from hydrido-, a thioether moiety having the structure R17-S (wherein the S is bound directly to a ring carbon of structure (III) such that R17 is attached to the phenyl ring of structure (III) via a thio linkage), or an electron-withdrawing substituent (such as nitro, acyl, formyl, sulfonyl, trifluoromethyl, cyano, chloro, and the like), R14 is selected from hydrido-, a thioether moiety having the structure R18-S (wherein the S is bound directly to a ring carbon of structure (III) such that R18 is attached to the phenyl ring of structure (III) via a thio linkage), an electron-withdrawing substituent (such as nitro, acyl, formyl, sulfonyl, trifluoromethyl, cyano, chloro, and the like), or ~O—C(O)—R19, wherein the tilde (~) denotes the bond to the ring carbon of structure (III) and R19 is selected from lower alkyl, modified lower alkyl, alkyl, modified alkyl, or aryl.

The group R15 is, in certain embodiments, selected from lower alkyl, modified lower alkyl, alkyl, modified alkyl, or aryl. In particular embodiments, R15 is selected from methyl, ethyl, n-propyl, isopropyl, n-butyl, iso-butyl, tert-butyl, or benzyl. In certain embodiments, the group R16 (if present), the group R17 (if present), and the group R18 (if present) are each independently selected from lower alkyl, modified lower alkyl, alkyl, modified alkyl, or aryl. In certain embodiments, the group R16 (if present), the group R17 (if present), and the group R18 (if present) are each independently selected from methyl, ethyl, n-propyl, isopropyl, n-butyl, iso-butyl, tert-butyl, or benzyl.

In certain embodiments in which R14 is ~C(O)—R19, R11 is located ortho or para to R14 (i.e. is bound to the ring at an ortho or para position relative to R14). In some such embodiments, R12 is located at the remaining ortho or para position (not occupied by R11) relative to R14, and R13 is located at one of the meta positions relative to R14. In some embodiments in which R14 is ~O—C(O)—R19, R12 and R13 are both located meta to R14. In certain embodiments in which R14 is ~O—C(O)—R19, the ring substituents located meta to R14 will typically be hydrido.

In certain embodiments in which R14 is a moiety selected from hydrido-, a thioether moiety having the structure R18-S, or an electron-withdrawing substituent, R11 is located meta to R14. In some such embodiments, R12 is located at the remaining meta position (not occupied by R11) relative to R14, and R13 is located ortho or para relative to R14. In some embodiments in which R14 is a moiety selected from hydrido-, a thioether moiety having the structure R18-S, or an electron-withdrawing substituent, R12 is located ortho or para to R14 and R13 is located at the remaining ortho or para position (not occupied by R12) relative to R14. In certain embodiments in which R14 is a moiety selected from hydrido-, a thioether moiety having the structure R18-S, or an electron-withdrawing substituent, the ring substituents located ortho and para to R14 will typically be hydrido.

With reference to structure (III), it should be noted that bonds (e.g., indicated by lines) that are directed into the center of a ring structure (e.g., benzene ring) mean that the bond can be to any one of the carbons of the ring that are only bonded to another carbon of the ring. It will further be understood that any carbon not bound to one of the explicitly drawn substituents of structure (III) (i.e. R11, R12, R13, R14, or the carbonate attached to the nucleotide) has a hydrido (not shown) bound to the carbon.

In addition to the groups described above, one of R11, R12, R13, or R14 may comprise a fluorescent moiety linked to the phenyl ring of structure (III) via a linker that is a substituent of the phenyl ring: for example, one of R15, R16, R17, or R18 may include an alkyl group having a fluorescent or colored moiety bound at one terminus of the alkyl group and bound to the ring via the sulfur linkage. In this embodiment, a fluorescence shift or color shift can be monitored upon cleavage of the protecting group from the active site hydroxyl. In this way, when the protecting group is removed, the reaction may be monitored by detecting a fluorescent or colored cleavage product. Examples of fluorescent and colorimetric species that may be employed include, but are not limited to: xanthenes such as fluoresceins, eosins and erythrosins, with preferred fluorescein compounds exemplified by 6-carboxyfluorescein, 5- and 6-carboxy-4,7-dichlorofluorescein, 2',7'-dimethoxy-5- and 6-carboxy-4,7-dichlorofluorescein, 2',7-dimethoxy-4',5'-dichloro-5- and 6-carboxyfluorescein 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein; rhodamines such as tetramethylrhodamine and Texas Red®; benzimidazoles; ethidiums; propidiums, anthracyclines; mithramycins; acridines; actinomycins; merocyanines; coumarins such as 4-methyl-7-methoxycoumarin; pyrenes; chrysenes; stilbenes; anthracenes; naphthalenes such as dansyl, 5-dimethylamino-1-naphthalenesulfonyl; salicylic acids; benz-2-oxa-1-diazoles (also known as benzofurans), including 4-amino-7-nitrobenz-2-oxa-1,3-diazole; fluorescamine; and 4-methylumbelliferone.

Referring still to structure (II), R2 is a phosphorus derivative that enables coupling to a free hydroxyl group of a nucleoside moiety (e.g. on a nascent polynucleotide molecule in the process of being synthesized). R2 has the structure (IV)

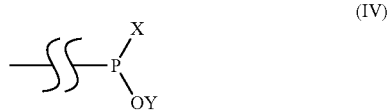

(IV)

wherein the groups are defined as follows:

X may be a halogen (such as —Cl or —Br) or a secondary amino group, —NQ1Q2. Certain phosphorus derivatives are phosphoramidites, where X is NQ1Q2, and in which Q1 and Q2 may be the same or different and are, in certain embodiments, selected from the group consisting of alkyl, aryl, aralkyl, cycloalkyl, alkenyl, cycloalkenyl, alkynyl, cycloalkynyl, optionally containing one or more nonhydrocarbyl linkages such as ether linkages, thio linkages, oxo linkages, amine, azole, and imine linkages, and optionally substituted on one or more available carbon atoms with a nonhydrocarbyl substituent such as cyano, nitro, halo, or the like. In certain embodiments, Q1 and Q2 represent lower alkyl, such as sterically hindered lower alkyls such as isopropyl, t-butyl, isobutyl, sec-butyl, neopentyl, tert-pentyl, isopentyl, sec-pentyl, and the like. In certain embodiments, Q1 and Q2 both represent isopropyl. Alternatively, Q1 and Q2 may be linked to form a mono- or polyheterocyclic ring having a total of from 1 to 3, usually 1 to 2 heteroatoms and from 1 to 3 rings. In such a case, Q1 and Q2 together with the nitrogen atom to which they are attached represent, for example, pyrrolidone, morpholino or piperidino. In certain embodiments, Q1 and Q2 have a total of from 2 to 12 carbon atoms. Examples of specific —NQ1Q2 moieties thus include, but are not limited to, dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine, and the like.

Y may be hydrido, hydrocarbyl or substituted hydrocarbyl), such as alkyl, alkenyl, aryl, aralkyl, or cycloalkyl, or substituted alkyl, alkenyl, aryl, aralkyl, or cycloalkyl. In certain embodiments, Y represents: lower alkyl; benzyl; substituted benzyl; electron-withdrawing β-substituted aliphatic, such as electron-withdrawing β-substituted ethyl such as β-trihalomethyl ethyl, β-cyanoethyl, β-sulfoethyl, β-nitro-substituted ethyl, and the like; electron-withdrawing substituted phenyl, such as halo-, sulfo-, cyano- or nitro-substituted phenyl; or electron-withdrawing substituted phenylethyl. In certain embodiments, Y represents methyl, β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethyethyl, 2-(4-pyridyl)ethyl, 2-(2-pyridyl)ethyl, allyl, 4-methylene-1-acetylphenol, β-thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)-ethyl, 1-methyl-1-phenylethyl, 3-buten-1-yl, 4-(trimethylsilyl)-2-buten-1-yl, cinnamyl, α-methylcinnamyl, and 8quinolyl.

The coupling reaction is, in certain embodiments, conducted under standard conditions used for the synthesis of oligonucleotides and conventionally employed with automated oligonucleotide synthesizers. Examples of such methodology are described in the pertinent texts and literature, e.g., in D. M. Matteuci et al. (1980) Tet. Lett. 521:719 and U.S. Pat. No. 4,500,707, the disclosure of such conditions in the latter of which are herein incorporated by reference. Coupling may be via any convenient coupling mechanism, e.g., phosphoramidite mediated coupling, H-phosphosphonate mediated coupling (Froehler, B. C. and Matteucci, M. D. Tetrahedron Letters (1986), 27(4), 469-72.), phosphodiester mediating coupling (Gilham and Khorana (1958) *J. Amer. Chem. Soc.* 80:6212), or phosphotriester mediated coupling (Narang et. al., (1980) *Methods in Enzymology* 65:610), to name some coupling mechanisms of interest.

The product of the coupling reaction may be represented as structural formula (V), as follows:

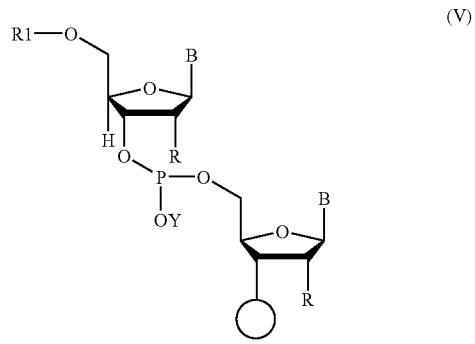

(V)

wherein B, R and Y are as defined earlier herein.

In the second step of the synthesis, the product (V) is treated with an alpha-effect nucleophile in order to oxidize the newly formed internucleoside linkage, oxidize a thioether group of the aryl carbonate protecting group, and remove the carbonate protecting group at the 5' terminus, thus converting the moiety —OR1 to —OH. The two step cycle of coupling and deprotection/oxidation steps are repeated as necessary to give an oligonucleotide having a desired sequence and length. The method may easily be adjusted for carrying out the synthesis either in the 3'-to-5' direction or in the 5'-to-3' direction. Advantageously, this step may be conducted in connection with fluorescent or other readily detectable protecting groups, enabling monitoring of individual reaction steps. Finally, because of the far more precise chemistry enabled by the present invention, the method readily lends itself to the highly parallel, microscale synthesis of oligonucleotides.

The product of this concurrent oxidation and deprotection step may thus be represented as follows (structure (VI)):

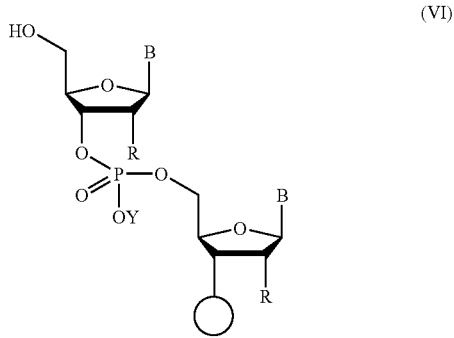

wherein Y is as defined earlier herein, and each B and each R are independently as defined earlier herein.

As explained earlier herein, the method of the invention also lends itself to synthesis in the 5'-to-3' direction. In such a case, the initial step of the synthetic process involves attachment of an initial nucleoside to a solid support at the 5' position, leaving the 3' position available for covalent binding of a subsequent monomer. The coupling reaction in which the nucleoside monomer becomes covalently attached to the 3' hydroxyl moiety of the support bound nucleoside is conducted under reaction conditions identical to those described for the 3'-to-5' synthesis. The coupling reaction is followed by treatment of the product with a combined oxidation/deprotection reagent in order oxidize the newly formed internucleoside linkage, to oxidize the thioether group of the carbonate protecting group, and to remove the hydroxyl protecting group at the 3' terminus, thus converting the moiety 3'-OR1 to 3'-OH. The two-step process of coupling and deprotection/oxidation is repeated until the oligonucleotide having the desired sequence and length is obtained. Following synthesis, the oligonucleotide may, if desired, be cleaved from the solid support.

The deprotection/oxidation reaction essentially may be conducted under the reported conditions used for the synthesis of polynucleotides as described in, e.g. U.S. Pat. No. 6,222,030 to Dellinger et al.; U.S. patent application Publ'n No. US2002/0058802 A1 to Dellinger et al.; Seio et al. (2001) Tetrahedron Lett 42 (49):8657-8660. As will be appreciated by those of ordinary skill in the art, given the disclosure herein, the conditions for the deprotection/oxidation step may vary depending on the nature of the protecting groups used. In order to be compatible with the carbonate protecting group provided for by the current invention, the conditions for the simultaneous deprotection and oxidation step (i.e. required conditions for release of the hydroxyl protecting group) may be selected to effectively oxidize the thioether group of the carbonate protecting group. Examples of conditions for the deprotection/oxidation reaction include a pH in the neutral to moderately basic range. In particular embodiments, the pH of the deprotection/oxidation reaction is about 6.0 or less, such as about 6.5 or less, including about 7.0 or less, such as about 7.5 or less, and the pH may be about 12 or less, such as about 11 or less, including about 10.5 or less, such as about 10 or less.

The combined deprotection/oxidation reagent may be selected to provide particularly advantageous synthesis conditions and characteristics, as are described herein. In an embodiment, the combined deprotection/oxidation reagent provides for contacting of the elongating polynucleotide chain with an alpha effect nucleophile under neutral or mildly basic aqueous conditions to remove reactive site hydroxyl protecting groups, concurrently oxidizing the thioether group of the carbonate protecting group to render the carbonate protecting group more labile under nucleophilic attack; the alpha effect nucleophile also serves to oxidize the phosphite triester linkage to a phosphotriester linkage.

In an embodiment, the combined deprotection/oxidation reagent provides a nucleophilic deprotection reagent under neutral or mildly basic conditions in aqueous solution. During the second step of the polynucleotide synthesis cycle (the deprotection/oxidation step), the product is treated with an "alpha effect" nucleophile in order to remove the protecting group at the reactive site hydroxyl (e.g. the 5' terminus), thus converting the moiety —OR1 to —OH. The alpha effect nucleophile also oxidizes the newly formed phosphite triester linkage to give the phosphotriester linkage The deprotection/oxidation reagent may be any compound or mixture of compounds that is compatible with the synthesis of polynucleotides and has the properties discussed herein. Typically, the deprotection/oxidation reagent includes a concentration of an oxidant that is high enough to rapidly oxidize the newly formed phosphite internucleotide linkage. In certain embodiments, the concentration is at least 0.1% vol/vol or higher, such as at least 0.5% vol/vol or higher, such as about 1.0% vol/vol or higher, e.g., about 3.0% vol/vol or higher. The concentration of the oxidant typically should be low enough to avoid appreciable (e.g. less than 1% per iteration of the synthesis cycle) amounts of oxidative destruction of the nucleobases or protected nucleobases. This concentration is typically less than 10% vol/vol, more typically less than 9% vol/vol, still more typically less than 7% vol/vol.

The deprotection/oxidation reagent in typical embodiments provides a source of a peroxyanion at neutral to mildly basic pH in the reaction mixture during the deprotection/oxidation reaction. The concentration of the peroxyanion will be related to the acid dissociation constant of the hydroperoxide species at equilibrium. The concentration of peroxyanion ranges from 0.01% to 99% of the total hydroperoxide concentration (i.e. sum of all hydroperoxide species, e.g. resonated and unprotonated forms), such as from 0.05% to 90% of the total hydroperoxide concentration, including from 0.1% to 50% of the total hydroperoxide concentration, e.g., from 1.0% to 30% of the total hydroperoxide concentration.

In certain embodiments, the nucleophilic deprotection reagent that exhibits an alpha effect is a peroxide or a mixture of peroxides. In certain embodiments, the pH at which the deprotection/oxidation reaction is conducted is generally in the range of about three pH units below the pKa of the nucleophilic deprotection reagent (that is, the pKa for formation of the corresponding peroxy anion) up to about three pH units above the pKa of the nucleophilic deprotection reagent. In certain embodiments, the pH of the deprotection/oxidation reaction is in the range of about one pH unit below the pKa of the nucleophilic deprotection reagent up to about pH 11. In certain embodiments, the pH will be the range that allows a high enough concentration of the peroxy anion to form, e.g. from about the pKa of the peroxide up to a pH of about 11. The peroxide may be either inorganic or organic. Suitable inorganic peroxides include those of the formula M+OOH—, where M+ is any counter ion, including for example H+, Li+, Na+, K+, Rb+, Cs+, or the like; and lithium peroxide or hydrogen peroxide and alkaline stabilized forms thereof can be particularly suitable. Suitable organic peroxides include those of the formula ROOH, where R is selected from the group consisting of alkyl, aryl, substituted alkyl, substituted aryl, and modified alkyl.

The α-effect nucleophiles can include, but are not limited to, peroxyanions, hydroxylamine derivatives, hydroximic acid and derivatives thereof, hydroximic acid and derivatives thereof, carbazide and semicarbazides and derivatives thereof. The α-effect nucleophiles can include compounds such as, but not limited to, hydrogen peroxide, peracids, perboric acid salts, alkylperoxides, hydrogen peroxide salts, hydroperoxides, butylhydroperoxide, benzylhydroperoxide, phenylhydroperoxide, cumene hydroperoxide, performic acid, peracetic acid, perbenzoic acid and substituted perbenzoic acids such as chloroperbenzoic acid, perbutyric acid, tertiary-butylperoxybenzoic acid, decanediperoxoic acid, other similar compounds, and corresponding salts, and combinations thereof. Hydrogen peroxide, salts of hydrogen peroxide and mixtures of hydrogen peroxide and performic acid are especially useful. Hydrogen peroxide, whose pKa is around 11, is particularly useful in solutions above pH 9.0. Below pH 9.0 there is no significant concentration of peroxyanion to work as an effective nucleophile. Below pH 9.0 it is especially useful to use mixtures of hydrogen peroxide and peracids. These peracids can be preformed and added to the solution or they can be formed in situ by the reaction of hydrogen peroxide and the carboxylic acid or carboxylic acid salt. An example is that an equal molar mixture of hydrogen peroxide and sodium formate can be used at pH conditions below 9.0 as an effective α-effect nucleophile solution where hydrogen peroxide alone is not provide a high concentration of α-effect nucleophiles. The utility of peracids tends to be dependent upon the pKa of the acid and size of molecule: the higher the pKa of the acid the more useful as a peroxyanion solution, the larger the size of the molecule the less useful. Typically the pKa of the peracid is lower than the pH of the desired peroxyanion solution.

The α-effect nucleophiles used in these reactions are, in certain embodiments, strong oxidants, and the concentration of the reagent in the solution is chosen in order to avoid oxidative side products where undesired. The α-effect nucleophiles are, in certain embodiments, less than 30% weight/vol of the solution, such as between 0.1% and 10% weight/vol of the solution and including 3% to 7% weight/vol of the solution. An example is a 3% solution of hydrogen peroxide is about 1 molar hydrogen peroxide. A solution of between 1 molar and 2 molar hydrogen peroxide is employed in certain embodiments. A solution of hydrogen peroxide and performic acid is an equal molar mixture of hydrogen peroxide and performic acid, both in the range of 1 to 2 molar, is employed in certain embodiments. An example of an in situ prepared solution of performic acid is 2 molar hydrogen peroxide and 2 molar sodium formate buffered at pH 8.5.

In certain embodiments, the α-effect nucleophile is chat as having a pKa in the range from about 4 to 13, about 4 to 12, about 4 to 11, about 5 to 13, about 5 to 12, about 5 to 11, about 6 to 13, about 6 to 12, about 6 to 11, about 7 to 13, about 7 to 12, or about 7 to 11.

It should also be noted that the dissociation constant (the pKa) is a physical constant that is characteristic of the specific α-effect nucleophile. Chemical substitution and solvent conditions can be used to raise or lower the effective dissociation constant and therefore specifically optimize the conditions under which the cleavage of the cleavable linker is performed (to result in release of the polynucleotide from the substrate, and, optionally, deprotection of groups protected by peroxyanion-labile protecting groups). In certain embodiments, appropriate selection of the α-effect nucleophile is made considering the other conditions of the method and the protecting groups of the polynucleotide. In addition, mixtures of carboxylic acids and hydroperoxides can be used to form salts of peracids in situ.

As an example a solution of hydrogen peroxide can be used with a solution of formic acid at pH conditions below 9.0. At pH conditions less than 9.0, hydrogen peroxide is not significantly ionized due to its ionization constant of around 11. At pH 7.0 only about 0.01% of the hydrogen peroxide is in the ionized form of the α-effect nucleophile. However, the hydrogen peroxide can react in situ with the formic acid to form performic acid in a stable equilibrium. At pH 7.0 the performic acid is significantly in the ionized form and is an active α-effect nucleophile. The advantage of such an approach is that solutions of performic acid tend to degrade rapidly and stabilizers need to be added. The equilibrium that is formed between the hydrogen peroxide solutions and the formic acid helps stabilize the performic acid such that it can be used to completely cleave the polynucleotides from the substrates prior to degrading. Performic acid is especially useful in a buffered mixture of hydrogen peroxide at pH 8.5 because the pKa of performic acid is approximately 7.1. Peracetic acid is useful at pH 8.5 but less useful than performic acid because the pKa of peracetic acid is approximately 8.2. At pH 8.5 peracetic acid is only about 50% anionic whereas at pH 8.5 performic acid is more than 90% anionic.

In general, the pKa for the hydroperoxides is about 8 to 13. The pKa for hydrogen peroxide is quoted to be about 10 to 12 depending upon the method of analysis and solvent conditions. The pKa for the alkylperoxides is about 8 to 14. The pKa for the peracids is about 3 to 9. In some embodiments in which the peroxyanion is hydroperoxide, the solution is at pH of about 9 to 11, e.g. at a pH of about 9 to about 10. In certain embodiments in which the peroxyanion is an alkylperoxide, the solution is at pH of about 8 to 11. In embodiments where the peroxyanion is a peracid, the solution is at pH of about 6 to 9. In addition, the peracid typically has a pKa of about 4 to 10.

In addition, the aqueous buffer solution may include a buffer, such as, but not limited to, tris(hydroxymethyl)aminomethane, aminomethylpropanol, citric acid, N,N'-Bis(2-hydroxyethyl)glycine, 2-[Bis(2-hydroxyethyl)amino]-2-(hydroxy-methyl)-1,3-propanediol, 2-(Cyclohexylamio)ethane-2-sulfonic acid, N-2-Hydroxyethyl)piperazine-N'-2-ethane sulfonic acid, N-(2-Hydroxyethyl)piperazine-N'-3-propane sulfonic acid, Morpholinoethane sulfonic acid, Morpholinopropane sulfonic acid, piperazine-N,N'-bis(2-ethane sulfonic acid), N-Tris(hydroxymethyl)methyl-3-aminopropane sulfonic acid, N-Tris(hydroxymethyl)methyl-2-aminoethane sulfonic acid, N-Tris(hydroxymethyl)methylglycine, and combinations thereof.

Aspects of the invention further include the nucleic acid products of the methods of the invention. The nucleic acid products, e.g., RNA, DNA, of the methods of the invention may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 20 to 25 monomeric units in length The product nucleic acids find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are iRNA nucleic acids, a variety of post-synthesis modifications may be desirable. The iRNA agent can be further modified so as to be attached to a ligand that is selected to improve stability, distribution or cellular uptake of the agent, e.g. cholesterol.

Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one stand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in PCT Application No. PCT/US2004/11829 filed Apr. 16, 2003.

An iRNA agent can include an internucleotide image (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a ZXY structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Ma. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar, O-AMINE and aminoalkoxy, $O(CH_2)NE$, (e.g., AMINE=$NH_2$; alkylamino, dialkylamio, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3) dinucleotide wherein the uridine is a 2'-modified nucleotide; at least one 5'-uridine-guanine-3' (5'-UG-3) dinucleotide, wherein the 5'-uridine is a 2'-modified nucleotide; at least one 5'-cytidine-adenine-3' (5'-CA-3) dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3) dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it Cleavage region means the nucleotides within 1, 2, or 3 nucleotides of the cleavage site, in either direction Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP—$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methalamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In certain embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)$_2$(O)P—O-5); 5'-diphosphate ((HO)$_2$(O)P—O—P(HO)(O)-5); 5'-triphosphate ((HO)$_2$(O)P—O—(HO)(O)P—O—P(HO)(O)O-5); 5'-guanosine cap (7-methylated or non-methylated) (7m-G-O-5'-HO)(O)P—O—(HO)(O)P—O—P(HO)(O)—O-5); 5'-adenosine cap (Appp), and any modified or unmodified nucleotide cap structure. Other suitable 5'-phosphate modifications will be known to the skilled person.

The sense strand can be modified in order to inactivate the sense stand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Where desired, the nucleic acid, e.g., iRNA, agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are dire to the same gene but different target sequences.

The present invention may be used to produce addressable arrays of different nucleic acids at predetermined known locations on a surface of a substrate. Arrays will contain multiple spots or features, such as from 100 to 100,000 features. All of the features may be different, or some or all could be the same. Each feature carries a predetermined polynucleotide having a particular sequence, or a predetermined mixture of polynucleotides.

In an execution of the present method, a polynucleotide is synthesized using one or more nucleoside phosphoramidites in one or more synthesis cycles having a) a coupling step, and b) a concurrent oxidation/deprotection step using the combined oxidation/deprotection reagent, as described above (with optional capping). In particular, the fabrication of each array 12 will be described. It will first be assumed that a substrate bound moiety is present at least at the location of each feature or region to be formed (that is, at each address). Such substrate bound moiety may, for example, be a nucleoside monomer which was deposited and deprotected at the location of each feature in a previous cycle, such that the deprotected reactive site hydroxyl is available for linking to another activated nucleoside monomer. Alternatively, the substrate bound moiety may be a suitable linking group previously attached to substrate 10. Both of these steps are known in in situ fabrication techniques. A droplet of a nucleoside phosphoramidite monomer solution is deposited onto the address and activated with a suitable activator (for example, a tetrazole, an imidazole, nitroimidazole, benzimidazole and similar nitrogen heterocyclic proton donors). In the case of phosphoramidites a non-protic low boiling point solvent could be used, for example, acetonitrile, dioxane, toluene, ethylacetate, acetone, tetrahydrofuran, and the like. Suitable activators for phosphoramidites are known and include tetrazole, S-ethyl tetrazole, dicyanoimidazole ("DCI"), or benzimidazolium triflate.

Any suitable droplet deposition technique, such as a pulse jet (for example, an inkjet head) may be used. The nucleoside phosphoramidite may be of as described above. Alternatively, DMT-O— could be on the 3' carbon and the phosphoramidyl group on the 5' carbon, if it was desired to have the polynucleotide grow in the 5' to 3' direction. Other protecting groups may be used such as those disclosed herein and as those commonly known in the art Any convenient reaction conditions may be used. The activated phosphoramidyl group will then couple the nucleoside monomer through a corresponding phosphite linkage with the substrate bound moiety (again, a linking group previously attached to substrate 10 or a deprotected nucleoside monomer deposited in a previous cycle). Particularly in the case of phosphoramidites, the reaction is complete very rapidly at room temperature of about 20° C. (for example, in one or two seconds).

At this point, a capping of substrate bound reactive site hydroxyls which failed to couple with a nucleoside compound may optionally be performed using known procedures.

The resulting compound can then be reacted with the combined oxidation/deprotection reagent composition. Such a composition should oxidize the phosphite linkage at a rate which is greater than the deprotection rate, as discussed above. For any particular proposed composition, oxidation rate can be evaluated by measuring the oxidation rate on phosphite coupled nucleosides using the same composition modified such that the phosphite is not destabilized. Deprotection rate can be measured with the proposed composition (optionally deleting the oxidizing agent) and the two rates compared. Examples of suitable compositions are listed below. In manufacture of an array, suitable times for exposure of the substrate to such solutions may range from about 10 to 60 seconds followed by washing with a non-aqueous solvent for about 10 to 60 seconds: Suitable solvents include aromatic solvents (such as benzene, xylene and particularly toluene) as well as chlorinated hydrocarbons (particularly chlorinated lower alkyl hydrocarbons such as dichloromethane).

The above steps can be repeated at each of many addresses on substrate 10 until the desired polynucleotide at each address has been synthesize. It will be understood however, that intermediate, washing and other steps may be required between cycles, as is well known in the art of synthesizing polynucleotides. Note though that since oxidation and deprotected on are accomplished with a single composition, no washes are required between such steps. Furthermore, as water may optionally be substantially eliminated, the thorough washing to remove water prior to the coupling step in the next cycle is not required or may be reduced. The cycles may be repeated using different or the same biomonomers, at multiple regions over multiple cycles, as required to fabricate the desired array or arrays on substrate.

Experimental

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

A. Preparation of 5'-thioether Substituted Aryl Carbonate Protected Deoxynucleosides 5'-thioether substituted aryl carbonate protected deoxynucleosides were prepared from the corresponding phenols in two steps. Phenylchloroformates were synthesized using phosgene, and then they were reacted with the nucleobase protected deoxynucleotides. The chloroformate was observed to be selective to the 5' hydroxyl, with only small quantities of the 3' product might being isolated.

1. Preparation of Thioether Phenols

Two commercially available alkylthiophenols, i.e., 4- and 2-(hydroxy)thioanisole (1a and 1b respectively), were purchased from Sigma-Aldrich, Milwaukee, Wis. USA. 4-Benzylthio-phenol (1c) was prepared in two different ways. 4-Mercaptophenol was alkylated with benzyl chloride or 4-iodophenol was substituted under Sandmayer conditions with benzylmercaptan (as described in F. Y. Kwong, S. L. Buchwald, Organic Letters, 4, 20, 3517-3520 (2002)). The previous reaction was preferred because it gave higher yield and used less odorous reagents. 2,4,6-(Trimethylthio)phenol (1d) was made by the CuI method. Careful preparation gave high yield without the need of chromatographic purification (Scheme 1).

SCHEME 1: Preparation of 4-benzylthiophenol and 2,4,6-trimethylthiophenol i: CuI, K$_2$CO$_3$, ethyleneglycol, iPrOH, ii: NaI, K$_2$CO$_3$, DMF, i*: CuI, K$_2$CO$_3$, DBU, ethyleneglycol, iPrOH.

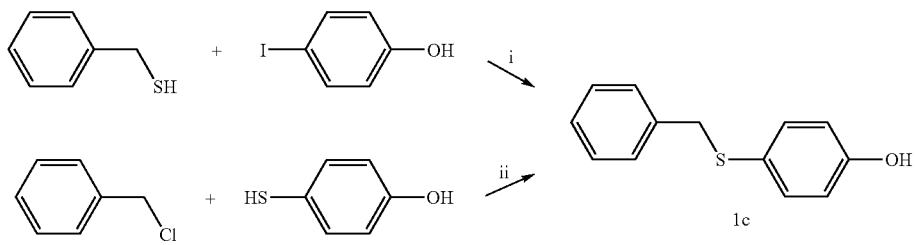

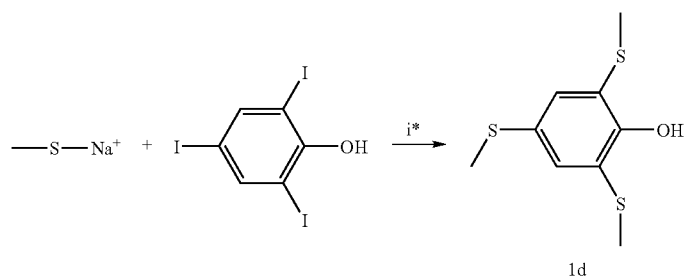

2. Synthesis of 5'-Thioether Substituted Aryl Carbonate-Thymidine Phosphoramidites All the four phenols were converted to their chloroformates and reacted with thymidine. The resultant 5'-protected thymidines (4-methylthio-(2a), 2-methylthio-(2b), 2,4,6-trimethylthio-(2d) and 4-benzylthio-ARCO T (2c) were converted to their phosphoramidites (3a-d) either with 2-cyanethyl-N,N,-diisopropyl-chlorophosphite or (bis-N,N-diisopropyl)-2-cyanoethyl-phosphoramidite reagents (Scheme 2).

SCHEME 2: Synthesis of thioaryloxycarbonyl T phosphoramidites i: phosgene, TEA then T, pyridine, ii: 2-cyanoethyl-N,N-diisopropyl-chlorophosphite reagent, DIEA, iii: bis-(N,N-diisopropyl)-2-cyanoethyl-phosphoramidite reagent, tetrazole.

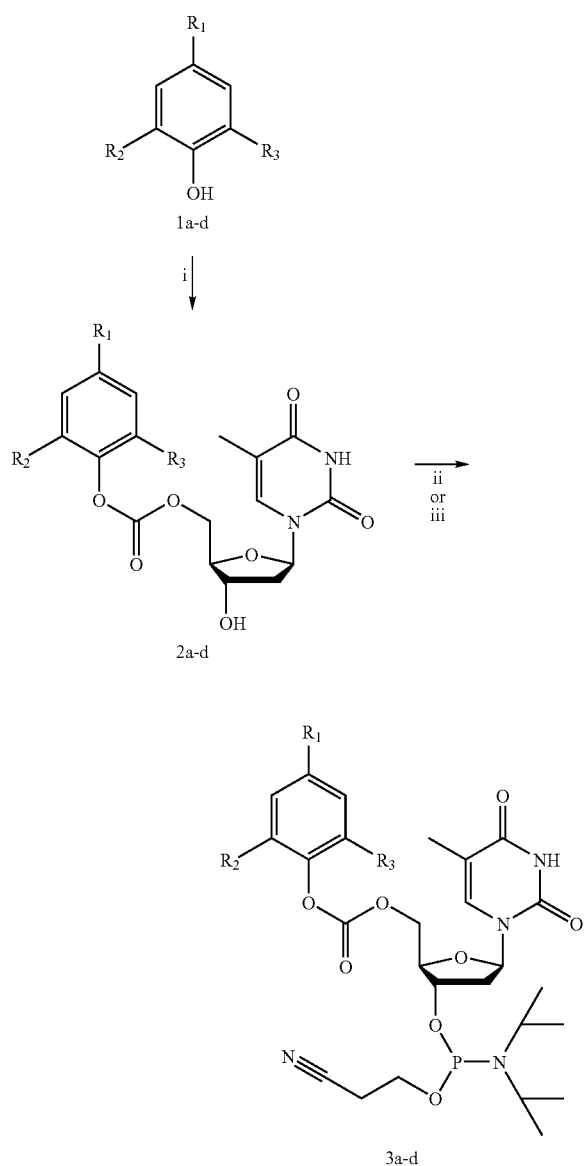

a: $R_1$=$CH_3S$, $R_2$=$R_3$=H
b: $R_1$=$R_3$=H, $R_2$=$CH_3S$
c: $R_1$=BnS, $R_2$=$R_3$=H
d: $R_1$=$R_2$=$R_3$=$CH_3S$

3. Optimization of the Coupling Step

Optimization of the coupling of the new phosphoramidites and the cleavage of the different thioether substituted aryl carbonate protections were performed on dT-succinyl-lcaa-CPG solid support using an Applied Biosystems 394 DNA/RNA synthesizer. The products were analyzed by RP-HPLC and LC-MS. The standard coupling cycle was modified. The coupling time was increased. The capping step was removed, and oxidation and DMT removal were replaced by the $H_2O_2$ oxidation/cleavage step. 12 oxidation solution at position 15 was replaced by different $H_2O_2$ mixtures and were pushed to columns for 10-30 seconds, then after a wait step (20-60 sec) $H_2O_2$ was repeatedly pumped through the synthesis columns. Aqueous MeOH and dry MeCN wash was applied after the oxidation/deprotection step.

In order to check the potential negative effect of the arylthio moiety on the efficacy of the phosphoramidite coupling, regular four-step poly T syntheses were performed, where a methylthioether moiety containing compound (thioanisole) was added to the DMT-T phosphoramidite solution (equivalent amount compared to the phosphoramidite). No change on the product profile was determined compared to the same authentic standard synthesis without thioanisole.

Next, the coupling efficiencies were optimized for the thioether substituted aryl carbonate protected monomers. 4-Methylthio-aryl carbonate T phosphoramidite was coupled to 5' free hydroxyl containing T-succinyl-lcaa-CPG with different activators like tetrazole (TET, 0.45 M), dicyanoimidazole (DCI, 0.25 M), ethylthio-1H-tetrazole (ETT, 0.5 M) and benzylthio-1H-tetrazole (BTT, 0.25 M). The activators were used as standard solutions for DNA synthesizers in different concentration in dry acetonitrile. Couplings were performed by the standard 1 µM CE cycle for different time durations (15, 25, 60 sec). The 5'-protecting group was removed by the treatment of $H_2O_2$ (6%, pH 8) and aq. cc. $NH_4OH$ (60° C., 2 h) that latter removed the remaining aryloxycarbonyl protection and the products from the solid support. The coupling yields were calculated using the peak areas of T and TpT peaks on the HPLC profile. Results are shown in FIG. 1. It was concluded that ethylthio-1H-tetrazole gave the fastest coupling, but 60 seconds is optimal for tetrazole too. Tetrazole is the most common and cheapest activator, thus it was used in the next experiments.

4. Optimization of the Deprotection/Oxidation Step

The pH of the hydrogen peroxide solution and time dependence of the cleavage of/for all the four prepared thioaryloxycarbonates were examined in a solid support model-system. Thioether substituted aryl carbonate protected TpT dimers attached to the support were synthesized by coupling the appropriate thioether substituted aryl carbonate protected T phosphoramidite to a 5' free hydroxyl T succinyl lcaa-CPG for 60 sec and then treated with either pH 7 or pH 8 aqueous $H_2O_2$— solution (6%) for 1-11 min. The non-deprotected 5'-thioaryloxycarbonyl TpT and the deprotected free 5'-hydroxyl TpT were cleaved from the support with aq. cc. $NH_4OH$ (room temperature, 2 h). This condition cleaves the succinyl solid support linkage and also the protecting group forming a TpT 5'-carbamate instead of 5'-hydroxyl (Scheme 3). From the ratio of the 5'-carbamate-TpT and the free 5'-hydroxyl-TpT products, the $H_2O_2$ deprotection yield and the needed cleavage time can be estimated. Results are shown in FIGS. 2A to 2D.

SCHEME 3: Deprotection of protecting group by aq. cc. NH₃ at different temperature.

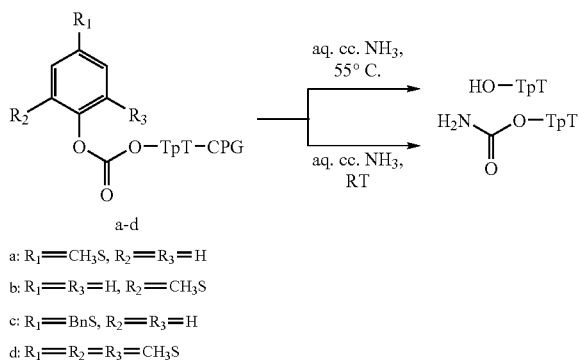

a: $R_1=CH_3S$, $R_2=R_3=H$
b: $R_1=R_3=H$, $R_2=CH_3S$
c: $R_1=BnS$, $R_2=R_3=H$
d: $R_1=R_2=R_3=CH_3S$

About 7 min is needed for complete deprotection with aq. $H_2O_2$ at pH 8 in case of 2- and 4-methylthio-aryl carbonate, 10 min for 4-benzylthio and hour scale for trimethylthio-aryl carbonate protecting groups. Using pH 7 hydrogen peroxide slowed down the cleavage and the curve shape for pH 7 changed, compared to pH 8 except for the 2-methylthio. The cleavage of the protecting group off the nucleotide has two steps: first is the oxidation of the sulfur to sulfoxide and the second is the hydrolisis of the carbonate bond by a nucleophilic attack of $HO_2$ anion. Both the oxidizing ability of $H_2O_2$ and the activity of the nuclephile anion changes with the pH. It is proved by NMR tube experiments that the rate-determining step at pH 8 is the oxidation. The NMR tube experiments were performed in a solution containing 6 mM 2-methylthio-aryl carbonate thymidine, 4.4 M $H_2O_2$ and 50% MeOH-d4. Only oxidation of the thioether to sulfoxide (ppm 2.39 2.79) was observed but no deprotection of the protecting group at pH 5.3 in 2 h. Deprotection occurred parallely with sulfur oxidation when using pH 8 solution mixture. Once the thioether is oxidized, the protecting group is removed but the non-oxidized thioether substituted aryl carbonate protecting group is very slowly hydrolized in a non-oxidizing aq. NaOH solution at pH 11 compared to the hydrolysis in a $H_2O_2$ solution at pH 8 (concentration of 15% aq. $HO_2^-$ at pH 8 is about the concentration of OH at pH 11 since $pK_a$ of $H_2O_2$ is 11.62). The oxidation is somewhat slower at pH 7 and the concentration of $HO_2^-$ is 10× less. The curves' shapes changed at pH 7, compared to pH 8. This and the NMR tube examinations support that the rate determining step becomes the hydrolysis at pH 7. The change of the reaction speed of the oxidation step is smaller than it is for the hydrolysis at a 10× less $HO_2^-$ concentration. The exception is the 2-methylthio containing protection, where the curve shapes are similar, which means the oxidation is fast enough as to remain the rate determining step. Altogether, it was concluded from the above experiments, that the 2-methylthio-aryl carbonate group is removed fastest (7 min) by 6% pH 8 $H_2O_2$ solution.

Finally, the cleavage solution was varied in order, to get higher cleavage yield in shorter time. The viscosity determines the flow rate in the synthesizer. Since acetonitrile has a very low viscosity (table 1) it is hard to find an aqueous-organic mixture with similar value. Furthermore, 50% acetonitrile/aq. $H_2O_2$ (pH:7-8) mixture loses almost a third of the $H_2O_2$-content of the starting 6% (m/v) in 1 day.

TABLE 1

| Viscosity values for liquids at 25° C.[3] | | | | | |
|---|---|---|---|---|---|
| Solvent | H₂O | MeCN | MeOH | Dioxane | IPrOH |
| Viscosity | 0.89 | 0.369 | 0.544 | 1.177 | 2.038 |

4-Methylthio-aryl carbonate-TpT-succinyl-lcaa-CPG was produced with 60 sec coupling and then treated for 3 min with a mixture of 50% (v/v) pH 8$H_2O_2$ solution (6% final percentage) and 50% (v/v) of the following organic solvents: MeCN, MeOH, dioxane, iPrOH and $H_2O$ as a control. The products were cleaved with aq. cc. NH₄OH (2 h, RT) and the TpT/TpT carbamate ratio was determined by HPLC analysis (FIG. 3).

The methanolic $H_2O_2$ mixture proved to be the most reliable not just because it produced high yield in the removal experiment, but it is the least viscous thus its transport in the synthesizer is the most reliable among the examined solutions.

B. Synthesis of Oligonucleotides $T_8$ syntheses were performed next, to prove the above optimization results on long sequences and also for further improvements in the yields. Thioether substituted aryl carbonate T monomers were used except the trimethylthio one, since its long cleavage time (~80 min) is not suitable for long DNA synthesis. Coupling was activated in all cases with tetrazole for 60 sec. Deprotection was performed with $H_2O_2$ (6% pH 9.1 50% methanol) for 12 min. The products were cleaved from support with aq. cc. NH₄OH solution at room temperature for 2 h, evaporated, redissolved in water and examined by HPLC.

The regular 4-step chemistry product was observed to contain small amounts of deletion sequences (mostly $T_7$) and some degradation sequences (e.g. $T_7$p) proved by LC-MS analysis. Methylthio-aryl carbonate synthesis was close to the results of the 4-step, but it also contained some $T_6$, $T_5$ and $T_4$, with their carbamates too. A very small amount of the $T_9$ was detected too, which may have resulted from amidite containing some free 5'-hydroxy contamination. 2-methylthio produced $T_8$ is comparable to the 4-step product.

$T_5$ syntheses were performed in case of the 4-benzylthio-ARCO T amidite and as a comparison with the 4-methylthio analogue. Using benzylthio-aryl carbonate T amidite, it was observed that the crude product contained more side-products, mainly $T_4$ and $T_6$ according to the LC-MS analysis.

Since the 2-methylthio-aryl carbonate protecting group seemed to be the most applicable on DNA synthesis, all the three remaining DNA phosphoramidites (dA, dG and dC) were prepared with that 5' protection using similar methods applied for the 2-methylthio-ARCO-T-amidite and standard protecting groups for the nucleobases, namely benzoyl for A and C and isobutiryl for G (Scheme 4).

SCHEME 4: Synthesis of dA$^{Bz}$, dG$^{ibu}$ and dC$^{Bz}$ phosphoramidite monomers, i: 2-methylthiophenol, phosgene, TEA then base-protected nucleoside, pyridine, ii: 2-cyanoethyl-bis-(N,N-diisopropyl) phosphite reagent, tetrazole in MeCN.

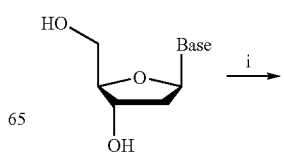

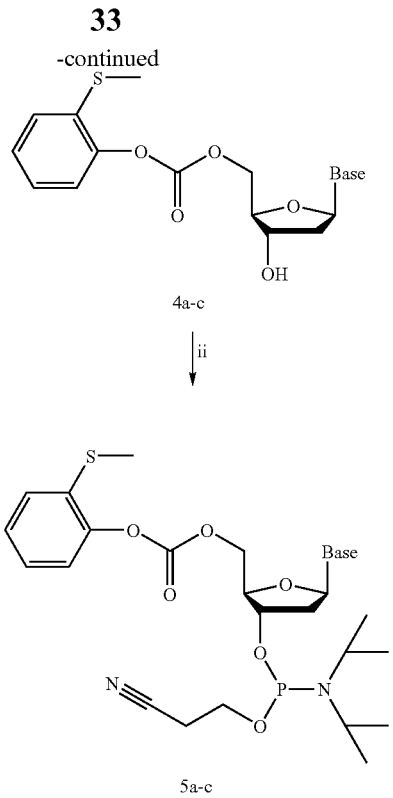

4a-c

↓ ii 5a-c

Base: a = N⁶-benzoyl-adenine
b = N²-isobutiryl-guanine
c = N⁴-benzoyl-cytidine

The applicability of the new monomers were examined on test sequences: (AT)₅ (SEQ ID NO:2), (GT)₅ (SEQ ID NO:3) (CT)₅ (SEQ ID NO:4) and on the ATG TCA ACT CGT CT (SEQ ID NO:01) sequence. DNAs were cleaved from the support with aq. cc. NH₄OH (60° C.). HPLC were obtained.

In these cases the question was how stable the exocyclic nucleobase amino protecting groups were under the oxidation/deprotection conditions. If the nucleobase protecting group is partially removed, branched DNAs may be formed, along with degradation products caused by the final aq. cc. NH₄OH treatment under the deprotection conditions (60° C. overnight). Isobutiryl on G has the longest half-life under basic conditions followed by the benzoyl on A and the shortest has the benzoyl on C. Based on the HPLC chromatograms, the slightly basic H₂O₂ treatment for 7×12 min did not remove the isobutiryl group from guanine but slightly removed the benzoyl from adenine and even more from cytidine, causing side-products in case of A and C containing mixed sequences.

There are more stable cytidine N⁴ protections, than benzoyl, like 2-methylbenzoyl or 2,4-dimethylbenzoyl⁴ but they are still too weak. 2,4,6-trimethylbenzoyl was not examined for this purpose, but it was expected to be even more stable. As the 2,4,6-trimethylbenzoyl chloride is commercially available, it was purchased and introduced on C to check its stability against H₂O₂ solutions. N6-anisoyl adenosine was also synthesized in order to have similarly stable base protection for A than for G. The sensitivity of these new protecting groups toward H₂O₂ solution was examined by HPLC kinetic experiments (Table 2).

TABLE 2

Stability of nucleoside base protections towards
H₂O₂ ($A^{Bz}$, $A^{An}$, $G^{iBu}$, $C^{Bz}$, $C^{iBu}$, $C^{TMBz}$)

| $t_{1/2}$ (min) | $A^{Bz}$ | $A^{An}$ | $G^{iBU}$ | $C^{Bz}$ | $C^{TMBz}$ |
|---|---|---|---|---|---|
| PH 6 | 438 | — | >1.3 day | 856 | — |
| PH 7 | 380 | — | >10 h | 268 | — |
| PH 8 | ~40 | ~180 | ~3 days | — | >1000 |
| 10% pH 8 | 17 | — | 655 | — | — |

Removal of anisoyl was slower than that of removal of benzoyl from adenine. No deprotection was observed for trimethylbenzoyl on C under the same conditions like for anisoyl A. Based on these examinations 5'-(2-methylthio-aryl carbonate) phosphoramidite monomers were synthesized from N⁶-anisoyl adenosine and N⁴-2,4,6-trimethylbenzoyl cytidine (Scheme 5).

SCHEME 5: Synthesis of $A^{An}$ and $C^{TMBz}$ phosphoramidite monomers, i: anisoyl chloride, pyridine, ii: 2,4,6-trimethylbenzoyl chloride, pyridine, iii: 2-methylthiophenol, phosgene, TEA then base-protected nucleoside, pyridine, iv: 2-cyanoethyl-bis(N,N-diisopropyl)-phosphite reagent, tetrazole in MeCN.

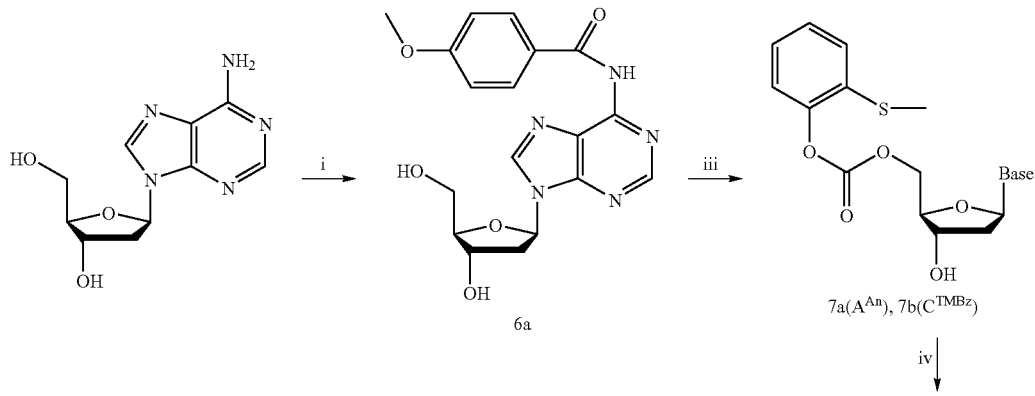

7a($A^{An}$), 7b($C^{TMBz}$)

iv ↓

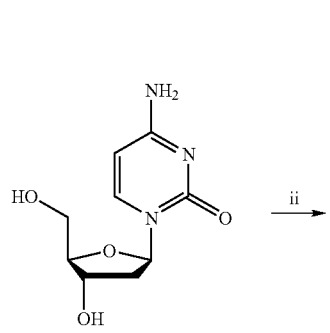 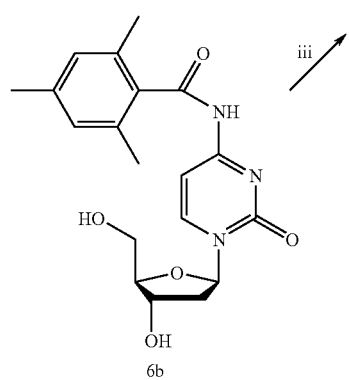 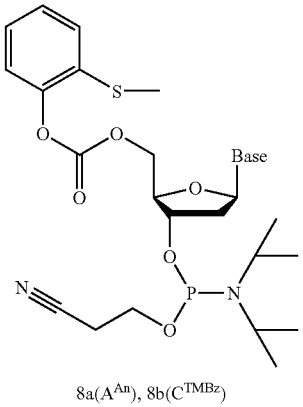

6b

8a($A^{An}$), 8b($C^{TMBz}$)

Alternating (CT)$_5$ (SEQ ID NO:4) (AT)$_5$ (SEQ ID NO:2) and the same mixed sequence ATGTCAACTCGTCT (SEQ ID NO:01) were synthesized by similar way as above with both the benzoyl and anisoyl protected adenosine monomer and with the TMBz-protected cytidine phosphoramidite. The HPLC results were compared.

In case of (CT)$_5$ (SEQ ID NO:4) prepared with the new protecting group, side product peaks are much smaller than in case of benzoyl. That supports the kinetic HPLC experiences where the TMBz group was very stable on C. Anisoyl adenosine produced a slightly nicer HPLC then the benzoyl protected one (oligomer (AT)$_5$ (SEQ ID NO:2)). The large peak before the main peak is always present in the case of using anisoyl protection, probably due to the extremely high extinction coefficient of anisoycamide. The HPLC chromatograms of the mixed sequences showed much better purity for the product than in case of using the regular nucleobase protections. It was observed that both the anisoyl and benzoyl groups can be used for the protection of adenosine.

The above results demonstrate that mixed DNA sequences were prepared in good purity with two-step DNA synthesis using 2-methylthioaryloxycarbonyl protected DNA monomers with $G^{ibu}$, $A^{Bz}$ and $C^{TMBz}$. The protecting groups employed above are displaced by assisted removal in two steps. The 2-methylthio-aryloxycarbonyl protecting group is fairly stable on 5'-hydroxyl in basic medium but when the sulfur is oxidized to sulfoxide it become sensitive to pH 9.1H$_2$O$_2$-solution. The nucleophilicity of H$_2$O$_2$ strong enough to partially remove the regular benzoyl protection on cytidine thus a new protecting group (TMBz) was developed and utilized. A 14mer mixed sequence DNA was prepared in good purity using the new phosphoramidite DNA monomers and a new, slightly basic, methanolic H$_2$O$_2$ oxidation/deprotection reagent.

Experimental
Abbreviations
Bz=benzoyl, An=anisoyl, iBu=isobutiryl, DPC=diphenylcarbamoyl, Ac=acetyl, TMBz=2,4,6-trimethylbenzoyl, MeCN=acetonitril, TEAB=triethylammonium bicarbonate, TEAAc=triethylammonium acetate, TEA=triethylamine, HFIP=1,1,1,3,3,3-hexafluoro-2-propanol, MQ water=Milli-Qplus purified HPLC grade deionized water, RT=room temperature, iPrOH=2-propanol, DIEA=N,N-diisopropylethyl amine, EtOAc=ethylacetate, ON=overnight, DBU=1,8-diazabicyclo[5.4.0]-undec-7-ene, DMSO=dimethyl sulfoxide, MeOH=methanol, DCI=dicyanoimidazole HPLC Experiments
Base Protection Stability.
200 µl 5% H$_2$O$_2$ (made from 30 wt % H$_2$O$_2$ solution in water, Sigma-Aldrich #216763 by 6× dilution then the pH was set to 7 or 8 with 1M NaOH) was added to 20 µl N-protected nucleobase in MeCN (saturated solution), and injected into HPLC system 1 at RT.
HPLC System 1:
Agilent 1100, BinPump G1312A, ALS G1329A, ALSTherm G1330B, COLCOM G1316A, DAD G1315B
Column: Agilent Hypersil ODS 5 µm, 4.0×250 mm, #799260D-584
Solvent A: 50 mM TEAB (pH 8.5) (made from 1.0 M buffer, Sigma #T7408), Solvent B: MeCN
Gradient: 1-20-50-60-100-100-1-1% B at 1-20-30-40-50-55-56-70 min.
HPLC System 2.
Agilent 1100, BinPump G1312A, ALS G1329A, ALSTherm G1330B, COLCOM G1316A, DAD G1315B
Column: Agilent Hypersil ODS 5 µm, 4.0×250 mm, #799260D-584
Solvent A: 50 mM TEAAc (pH 7.1) (made from 2.0 M buffer, GlenResearch #60-4110-62), Solvent B: MeCN
Gradient: 1-20-50-60-100-100-1-1% B at 1-20-30-40-50-55-56-70 min.
HPLC System 3:
Agilent 1100, CapPump G1376A, 1-WPS G1377A, ALSTherm G1330B, COLCOM G1316A, DAD G1315B
Column: Agilent Zorbax SB-C18 5 µm, 0.5×150 mm, #DE44F01348, Guard: 0.5×35 mm #DE43H00058
Solvent A: 0.4 M HFIP/2.2 mM TEA (pH 6.9) (made from 100 g HFIP, Aldrich #105228, 455 µl TEA diluted with MQ water to a total volume of 1488 ml), Solvent B: MeOH
Gradient: 0-30-100-100-0-0% B at 0-60-95-120-121-150 min.
MS System:
PE SCIEX API QSTAR PULSAR
TLC system A: 20% EtOAc/hexanes B: 50:45:45:5 hexanes/CH$_2$Cl$_2$/EtOAc/TEA C: 50% CH$_2$Cl$_2$/hexanes D: 10% MeOH/CH$_2$Cl$_2$, E: 50:45:45:10 hexanes/CH$_2$Cl$_2$/EtOAc/TEA, F: 1:1:2:0.4 hexanes/CH$_2$Cl$_2$/EtOAc/TEA, G: 50:45:45:10:2 hexanes/CH$_2$Cl$_2$/EtOAc/TEA/MeOH Synthesis method 1: forming 5'-ARCO protected-2'-deoxynucleotides (2a-d or 4a-c or 7a-b) Substituted phenol (1a-d) (20 mmol) was dissolved in abs. toluene (50 ml) and was added to an ice cold solution of phosgene in toluene (20%, 50 ml, 100 mmol) followed by the addition of TEA (3.6 ml, 25.7 mmol) in 15 ml abs. toluene. The reaction mixture was stirred in argon for 2 h, while it was warmed up to RT. Solvents were evaporated and the residue was suspended in ether and filtered in argon in a Schlenk funnel. Evaporation again resulted in the oil of phenyl chloroformate that was dissolved in abs. $CH_2Cl_2$ (50 ml) and was added to a cooled (−78° C.), frozen solution of dry 2'-deoxy-nucleoside (16 mmol). The reaction mixture was shaken by hand until everything dissolved and stirred ON. Solvents were then removed and the resulting oil was extracted: EtOAc (300 ml)/$KHSO_4$ (200 and 100 ml), $NaHCO_3$ (200 ml) and brine (200 ml). EtOAc was dried ($Na_2SO_4$), filtered and evaporated to give crude product, which was purified by chromatography.

Synthesis method 2a: forming 5'-ARCO protected-2'-deoxynucleotide phosphoroamidites (3a-d) 5'-ARCO protected-2'-dedxynucleotide (2a-d) (8.1 mmol) was dissolved in $CH_2Cl_2$ (50 ml), chlorophosphite reagent (2.72 ml, 12.2 mmol) and DIEA (2.28 ml, 13 mmol) was added under argon gas. The reaction is complete in 1 h. Evaporation and chromatography (1:1:2 hexanes/$CH_2Cl_2$/EtOAc) on TEA neutralized silica gel gave the pure product. Silica gel (500 ml) was neutralized with hexanes/$CH_2Cl_2$/EtOAc/TEA (500 ml, 50:45:45:20) and washed with hexanes/$CH_2Cl_2$/EtOAc (600 ml, 50:45:45).

Synthesis method 2b: forming 5'-ARCO protected-2'-deoxynucleotide phosphoroamidites (3a-b or 5a-c or 8a-b) 5'-ARCO protected-2'-deoxynucleotide (2a-b or 4a-c or 7a-b) (9.5 mmol) was dissolved in abs. $CH_2Cl_2$ (200 ml) under argon gas and bisamidite reagent (4.6 ml, 9.5 mmol) was added followed by the addition of tetrazole in abs. MeCN (17 ml, 0.45 M, 7.6 mmol) or DCI (0.898 g, 7.6 mmol). The reaction is complete in 8 hours. Evaporation and chromatography (1:1:2 hexanes/$CH_2Cl_2$/EtOAc) on TEA neutralized silica gel gave the pure product.

5'-O-[4-(Methylthio)phenoxy]carbonyl-2'-deoxy thymidine (2a) Preparation with synthesis method 1 from 24.5 mmol 2'-deoxy thymidine gave the product, which was purified by chromatography (0-5% MeOH/$CH_2Cl_2$). Yield 6.51 g (66%). TLC $R_f$ (D) 0.36. $^1$H NMR (DMSO-$d_6$) δ 11.33 (s, 1H), 7.48 (s, 1H), 7.28 (m, 2H), 7.18 (m, 2H), 6.20 (t, J=7 Hz, 1H), 5.48 (d, J=4 Hz, 1H), 4.44-4.32 (m, 2H), 4.29 (m, 1H), 3.97 (m, 1H), 2.46 (s, 3H), 2.22-2.07 (m, 2H), 1.75 (s, 3H). $^{13}$C NMR δ 164.39, 153.62, 151.14, 148.83, 136.65, 136.59, 127.74, 122.51, 110.49, 84.56, 83.90, 70.74, 68.87, 39.16, 15.73, 12.84. MS (−ESI, +Cl$^−$) calcd for $C_{18}H_{20}ClN_2O_7S$ 443.068 found 443.0662 (4.0 ppm). The above chromatography yielded in 3'-O-[4-(methylthio)phenoxy]carbonyl-2'-deoxy thymidine also: 0.294 g (3%). TLC $R_f$ (D) 0.38. $^1$H NMR (DMSO-$d_6$) δ 11.37 (s, 1H), 7.73 (s, 1H), 7.29 (m, 2H), 7.24 (m, 2H), 6.21 (m, 1H), 5.25 (m, 2H), 4.16 (m, 1H), 3.64 (m, 2H), 2.47 (s, 3H), 2.49-2.29 (m, 2H), 1.77 (s, 3H). $^{13}$C NMR δ 164.36, 153.11, 151.19, 148.83, 136.59, 136.48, 127.69, 122.62, 110.50, 84.79, 84.30, 80.33, 62.04, 36.98, 15.75, 12.99. MS (−ESI, +Cl$^−$) calcd for $C_{18}H_{20}ClN_2O_7S$ 443.068 found 443.0669 (2.5 ppm).

5'-O-[4-(Methylthio)phenoxy]carbonyl-3'-O-[(2-cyanoethyloxy)-N,N-(diisopropyl)amino-phosphityl]-2'-deoxy thymidine (3a) Using synthesis method 2a, compound (2a) (3.0 g, 7.3 mmol) in $CH_2Cl_2$ (80 ml), chlorophosphite reagent (2.46 ml, 11.0 mmol) and DIEA (2.05 ml, 11.8 mmol) gave the product that was purified with chromatography on neutralized silica gel with 50:45:45:21 hexanes/$CH_2Cl_2$/EtOAc/DIEA (3.8 g, 85%). Using synthesis method 2b we isolated the product in 62% yield. TLC $R_f$ (E) 0.25, 0.35 (diastereomer pair). $^{31}$P NMR ($CD_3CN$) δ 149.63, 149.49. $^1$H NMR ($CD_3CN$) δ 9.1 (bs, 1H), 7.39 (m, 1H), 7.3 (m, 2H), 7.15 (m, 2H), 6.24 (m, 1H), 4.59 (m, 1H), 4.51-4.36 (m, 2H), 4.28-4.22 (m, 1H), 3.88-3.72 (m, 2H), 3.67-3.59 (m, 2H), 2.67 (t, J=7 Hz, 2H), 2.48 (s, 3H), 2.44-2.18 (m, 2H), 1.81 (s, 3H), 1.2 (m, 12H). $^{13}$C NMR δ 163.92, 153.55, 150.66, 148.90, 148.88, 136.04, 135.99, 130.20, 127.56, 121.99, 121.97, 116.21, 110.79, 110.75, 84.98, 84.95, 83.24, 83.20, 73.33, 73.18, 73.16, 73.01, 67.87, 67.72, 58.76, 58.56, 43.40, 43.37, 43.27, 43.24, 38.60, 38.56, 24.17, 24.14, 24.10, 24.07, 24.03, 24.00, 20.30, 20.28, 20.21, 15.32, 11.84. MS (−ESI, +Cl$^−$) calcd for $C_{27}H_{37}ClN_4O_8P$ 643.1759 found MS 643.1764 (0.8 ppm).

5'-O-[2-(Methylthio)phenoxy]carbonyl-2'-deoxy thymidine (2b) Preparation with synthesis method 1 from 24.5 mmol 2'-deoxy thymidine gave the product, which was purified by chromatography (0-5% MeOH/$CH_2Cl_2$). Yield 4.86 g (49%). TLC $R_f$ (D) 0.47. $^1$H NMR (DMSO) δ 11.34 (s, 1H), 7.48 (s, 1H), 7.37-27 (m, 2H), 7.21 (m, 2H), 6.21 (t, J=7 Hz, 1H), 5.49 (d, J=4 Hz, 1H), 4.46-4.36 (m, 2H), 4.27 (m, 1H), 3.98 (m, 1H), 2.41 (s, 3H), 2.21-2.08 (m, 2H), 1.75 (s, 3H). $^{13}$C NMR δ 164.38, 153.07, 151.13, 147.97, 136.59, 131.98, 127.92, 127.39, 126.56, 122.71, 110.53, 84.55, 83.97, 70.73, 69.13, 39.17, 14.67, 12.86. MS (−ESI, +Cl$^−$) calcd for $C_{18}H_{20}ClN_2O_7S$ 443.068 found 443.0702 (4.9 ppm).

5'-O-[2-(Methylthio)phenoxy]carbonyl-3'-O-[(2-cyanoethyloxy)-N,N-(diisopropyl)amino-phosphityl]-2'-deoxy thymidine (3b) Using synthesis method 2a, compound (2b) (4.7 g, 11.5 mmol) in $CH_2Cl_2$ (100 ml), chlorophosphite reagent (3.84 ml, 17.25 mmol) and DIEA (3.2 ml, 18.4 mmol) gave the product that was purified with chromatography on neutralized silica gel with 1:1:2 hexanes/$CH_2Cl_2$/EtOAc (6.9 g, 99%). Using synthesis method 2b, the product was isolated in 73% yield. TLC $R_f$ (D) 0.24, 0.36 (diastereomer pair). $^{31}$P NMR ($CD_3CN$) δ 149.80, 149.64. $^1$H NMR δ 9.26 (bs, 1H), 7.38-7.15 (m, 5H), 6.24 (m, 1H), 4.60 (m, 1H), 4.48 (m, 2H), 4.28-4.22 (m, 1H), 3.88-3.72 (m, 2H), 3.69-3.58 (m, 2H), 2.67 (t, J=6 Hz, 2H), 2.44 (s, 3H), 2.42-2.18 (m, 2H), 1.81 (s, 3H), 1.2 (m, 12H). $^{13}$C NMR δ 163.96, 153.02, 150.68, 148.13, 135.99, 135.94, 131.94, 127.52, 127.29, 127.23, 126.28, 122.20, 118.85, 110.81, 110.77, 84.95, 84.91, 83.36, 83.29, 83.25, 82.98, 82.92, 73.24, 73.12, 73.07, 72.94, 72.88, 68.14, 67.98, 58.83, 58.79, 58.64, 58.59, 43.41, 43.38, 43.29, 43.26, 38.64, 38.61, 24.17, 24.14, 24.07, 24.01, 20.28, 20.23, 20.21, 14.34, 14.32, 12.43. MS (−ESI, +Cl$^−$) calcd for $C_{27}H_{37}ClN_4O_8P$ 643.1759 found 643.1728 (4.8 ppm).

4-Benzylsulfanyl-phenol (1c) Method b: Thiophenole (2.79 g, 22 mmol) was dissolved in abs. DMF (50 mol), benzyl chloride (3.8 ml, 33 mmol), NaI (4.9 g, 33 mmol) and $K_2CO_3$ (7.6 g, 55 mmol) was added. The suspension was warmed up to 110° C. and stirred for 18 h. The solvent was evaporated from the cooled mixture. The oily residue was then suspended in EtOAc (200 ml) and washed with water (200 ml), $NaHSO_4$ (200 ml). The combined aqueous phase (pH 3) was extracted with EtOAc (200 ml). The organic phases were combined and dried with $Na_2SO_4$, filtered and evaporated. Chromatography (4-10% EtOAc/hexanes) resulted in 2.94 g (61.5%) pure product TLC $R_f$ (A) 0.50. $^1$H NMR ($CD_3CN$) δ 7.2 (m, 7H), 6.7 (m, 2H), 4.8 (bs, 1H), 4.01 (s, 2H). $^{13}$C NMR δ 156.76, 138.75, 133.97, 129.06, 128.52, 127.13, 125.05, 116.04, 40.27. MS (−ESI, M−H$^+$) calcd for $C_{13}H_{11}OS$ 215.0531 found 215.0544 (6.2 ppm) and side products [1-benzyloxy-4-benzylsulfanyl-benzene: 0.42 g, 6%. TLC $R_f$ (A) 0.81. $^1$H NMR ($CD_3CN$) δ 7.4-7.2 (m, 12H), 6.86 (m, 2H), 5.04 (s, 2H) and 4-benzyloxy-benzenethiol].

Method a: Iodophenol (8.4 g, 38 mmol) was dissolved in iPrOH then benzyl mercaptan (4.95 ml, 38 mmol), $K_2CO_3$ (10.6 g, 76 mmol), CuI (364 mg, 1.9 mmol) and ethylene glycol (4.28 ml, 76 mmol) was added and stirred under argon at 45° C. 22 h. The solvents were evaporated and the residue was suspended in water (400 ml) and the pH was set to 2. The suspension was extracted with EtOAc (2×250 ml), dried with Na$_2$SO$_4$, filtered and evaporated. The product was purified by chromatography (4% EtOAc/hexanes) resulting pure 1c in 1.87 g (22.6%).

5'-O-[4-(Benzylthio)phenoxy]carbonyl-2'-deoxy thymidine (2c) 4-Benzylsulfanyl-phenyl-chloroformate was made by synthesis method 1 from 4-benzylsulfanyl-phenol (1c) (2.07 g, 9.6 mmol) with phosgene solution (20% in toluene, 24 ml, 48 mmol) and TEA (1.75 ml, 12.5 mmol) in abs. CH$_2$Cl$_2$ (10 ml). Yield: 2.6 g (100%). $^1$H NMR δ (CDCl$_3$) 7.3-7.1 (m, 9H), 4.11 (s, 2H). $^{13}$C NMR δ 150.2, 149.6, 138.1, 135.9, 131.1, 129.2, 128.4, 127.5, 121.0, 39.2. 4-Benzylsulfanyl-phenyl-chloroformate (2.6 g, 9.6 mmol) in abs. CH$_2$Cl$_2$ (20 ml), dried 2'-deoxythymidine (2.2 g, 9.1 mmol) in abs. pyridine (200 ml). Chromatography (0-6% MeOH/CH$_2$Cl$_2$). Product is 1.55 g (35%). TLC R$_f$(A) 0.67. $^1$H NMR (DMSO-d$_3$) δ 11.37 (s, 1H), 7.50 (s, 1H), 7.40-7.35 (m, 4H), 7.32-7.29 (m, 2H), 7.23 (m, 1H), 7.19 (m, 2H), 6.23 (t, J=7 Hz, 1H), 5.51 (bs, 1H), 4.46-4.35 (m, 2H), 4.31 (m, 1H), 4.26 (s, 2H), 3.99 (m, 1H), 2.16 (m, 2H), 1.77 (s, 3H). $^{13}$C NMR δ 164.38, 153.49, 151.13, 149.57, 138.00, 136.65, 134.52, 130.26, 129.50, 129.08, 127.80, 122.51, 110.50, 84.55, 83.88, 70.73, 68.89, 39.14, 37.59, 12.84. HRMS (−ESI, M+Cl$^−$) calculated for C$_{24}$H$_{24}$ClN$_2$O$_7$S 519.0993 found 519.1000 (1.3 ppm). The 3' product was also isolated: 0.13 g (3%) $^1$H NMR (DMSO) δ 11.36 (s, 1H), 7.73 (s, 1H), 7.37-7.13 (m, 9H), 6.21 (m, 1H), 5.24 (m, 1H), 4.44 (m, 1H), 4.23 (s, 2H), 4.15 (m, 1H), 3.63 (m, 2H), 2.4-2.3 (m, 2H), 1.76 (s, 3H).

5'-O-[4-(Benzylthio)phenoxy]carbonyl-3'-O-[2-(cyanoethyl)oxy-N,N-(diisopropyl)amino-phosphityl]-2'-deoxy thymidine (3c) Using synthesis method 2, compound (2c) (1.28 g, 2.6 mmol) in CH$_2$Cl$_2$ (30 ml), chlorophosphite reagent (0.884 ml, 3.9 mmol) and DIEA (0.735 ml, 4.2 mmol) gave pure product (1.6 g, 88%) after quick chromatography. TLC R$_f$(B) 0.32. $^{31}$P NMR (CD$_3$CN) δ 149.91, 149.88. $^1$H NMR δ 11.38 (s, 1H), 7.49 (s, 1H), 7.37-7.32 (m, 4H), 7.27 (m, 2H), 7.21 (m, 1H), 7.14 (m, 2H), 6.20 (m, 1H), 4.56 (m, 1H), 4.49-4.35 (m, 2H), 4.22 (s, 2H), 4.13 (m, 1H), 3.75 (m, 2H), 3.58 (m, 2H), 2.77 (m, 2H), 2.37-2.24 (m, 2H), 1.75 (s, 3H), 1.14 (d, J=7 Hz, 12H). $^{13}$C NMR δ 164.36, 153.40, 151.09, 149.58, 149.54, 137.97, 136.79, 136.71, 134.57, 130.28, 129.48, 129.07, 127.79, 122.46, 122.44, 119.71, 110.63, 110.58, 84.92, 84.88, 83.05, 83.01, 82.66, 82.61, 73.68, 73.51, 73.45, 73.28, 68.45, 68.29, 59.09, 58.91, 43.45, 43.42, 43.30, 38.17, 38.13, 37.65, 25.05, 25.00, 24.94, 24.86, 20.55, 20.48, 12.81. MS (−ESI, M+Cl$^−$) calcd for C$_{33}$H$_{41}$ClN$_4$O$_8$PS 719.2072 found 719.2043 (4.0 ppm).

2,4,6-Tris-methylsulfanyl-phenol (1d) 2,4,6-Triiodo phenol (11.4 g, 24 mmol) and ethylene glycol (2.66 ml, 48 mmol) was added to a solution of DBU (3.55 ml, 24 mmol) in iPrOH (250 ml) and degassed with argon for 20 min. CuI (4.56 g, 24 mmol) and NaSCH$_3$ (11 g, 156 mmol) was then added to the above solution and immediately warmed up to 95° C. and was stirred ON in argon. The solvents were then evaporated off and the residue was suspended in EtOAc and filtered through a 4×6 cm silica gel pad and washed with EtOAc (500 ml). The solution was evaporated again, dissolved in CH$_2$Cl$_2$ and filtered again on a same size silica pad, washed with 50% hexanes/CH$_2$Cl$_2$ (500 ml). Evaporation gave 4.6 g (82%) product, which crystallized in the freezer. TLC R$_f$(C) 0.28. $^1$H NMR (CDCl$_3$) δ 7.2 (s, 2H), 6.96 (s, 1H), 2.48 (bs, 3H), 2.40 (bs, 6H). $^{13}$C NMR (CDCl$_3$) δ 152.15, 130.25, 129.78, 123.49, 18.33, 17.83. MS (+ESI, M+H$^+$) calcd for C$_9$H$_{13}$OS$_3$ 233.012825 found 233.0327.

5'-O-[2,4,6-(Trimethylthio)phenoxy]carbonyl-2'-deoxy thymidine (2d) Preparation with synthesis method 1 gave 5.8 g crude product, which was then purified by chromatography (0-5% MeOH/CH$_2$Cl$_2$). Yield 4.52 g (55%). TLC R$_f$(D) 0.48.

$^1$H NMR (DMSO) δ 11.33 (s, 1H), 7.48 (s, 1H), 6.92 (s, 2H), 6.21 (t, J=8 Hz, 1H), 5.50 (d, J=5 Hz, 1H), 4.47-4.37 (m, 2H), 4.26 (m, 1H), 3.96 (m, 1H), 2.53 (s, 3H), 2.43 (s, 6H), 2.21-2.0 (m, 2H), 1.75 (s, 3H). $^{13}$C NMR δ 164.37, 152.17, 151.14, 141.42, 138.63, 136.58, 133.70, 120.27, 110.53, 84.56, 83.99, 70.72, 69.43, 39.15, 15.60, 14.70, 12.88. MS (−ESI, +Cl$^−$) calcd for C$_{20}$H$_{24}$ClN$_2$O$_7$S$_3$ 535.0435 found 535.0429 (1.1 ppm).

5'-O-[2,4,6-(Trimethylthio)phenoxy]carbonyl-3'-O-[(2-cyanoethyloxy)-N,N-(diisopropyl)amino-phosphityl]-2'-deoxy thymidine (3d) Using synthesis method 2a, compound (2d) (4.08 g, 8.1 mmol) in CH$_2$Cl$_2$ (50 ml), chlorophosphite reagent (2.72 ml, 12.2 mmol) and DIEA (2.28 ml, 13 mmol) gave the product that was purified on neutralized silica gel with 1:1:2 hexanes/CH$_2$Cl$_2$/EtOAc (5.7 g, 95%). TLC R$_f$(E) 0.26, 0.35 (diastereomer pair). $^{31}$P NMR (CD$_3$CN) δ 149.82, 149.71. $^1$H NMR δ 9.34 (bs, 1H), 7.39 (m, 1H), 6.96 (s, 2H), 6.25 (m, 1H), 4.57 (m, 1H), 4.48 (m, 2H), 4.25 (m, 1H), 3.86-3.72 (m, 2H), 3.68-3.59 (m, 2H), 2.67 (t, J=7 Hz, 2H), 2.52 (s, 3H), 2.44 (s, 6H), 2.42-2.18 (m, 2H), 1.82 (s, 3H), 1.19 (d, J=7 Hz, 12H). $^{13}$C NMR δ 164.01, 152.17, 152.14, 150.71, 141.77, 138.78, 136.03, 135.98, 133.60, 120.47, 120.42, 118.83, 110.81, 110.76, 84.95, 84.90, 83.28, 83.24, 82.98, 82.91, 73.07, 72.94, 72.89, 72.77, 68.43, 68.25, 67.80, 58.88, 58.81, 58.69, 58.62, 43.41, 43.38, 43, 28, 43.26, 38.64, 24.19, 24.16, 24.09, 24.03, 20.31, 20.28, 20.24, 20.22, 15.21, 14.39, 11.96. MS (−ESI, +Cl$^−$) calcd for C$_{29}$H$_{41}$ClN$_4$O$_8$PS$_3$ 735.1513 found 735.1520 (0.95 ppm).

5'-O-[2-(Methylthio)phenoxy]carbonyl-N$^6$-benzoyl-2'-deoxy adenosine (4a) Preparation with synthesis method 1 from N$^6$-benzoyl-2'-deoxy adenosine (5 g, 14.1 mmol) gave the crude product (4.9 g, 67%), which was purified by chromatography (0.5-3.5% MeOH/CH$_2$Cl$_2$). Yield 2.0 g (27%). TLC R$_f$(D) 0.5. $^1$H NMR (DMSO-d$_6$) δ 11.22 (s, 1H), 8.75 (s, 1H), 8.64 (s, 1H), 8.03 (d, J=7 Hz, 2H), 7.63 (t, J=7 Hz, 1 H), 7.54 (t, J=7 Hz, 2H), 7.34-7.25 (m, 2H), 7.21-7.15 (m, 2H), 6.53 (t, J=7 Hz, 1H), 5.62 (d, J=4 Hz, 1H), 4.58 (m, 1H), 4.57-4.39 (m, 2H), 4.14 (m, 1H), 2.89 (m, 1H), 2.44 (m, 1H), 2.38 (s, 3H). $^{13}$C NMR δ 166.32, 153.03, 152.58, 152.37, 151.11, 148.00, 143.82, 134.01, 133.16, 131.99, 129.19, 129.17, 127.86, 127.40, 126.59, 126.55, 122.72, 84.67, 84.39, 71.16, 69.23, 39.13, 14.68. MS (−ESI, +Cl$^−$) calcd for C$_{25}$H$_{23}$ClN$_5$O$_6$S 556.1058 found 556.1066 (1.4 ppm).

5'-O-[2-(Methylthio)phenoxy]carbonyl-N$^2$-isobutyryl-2'-deoxy guanosine (4b) Preparation with synthesis method 1 from N$^2$-isobutiryl-2'-deoxy guanosine (5 g, 14.8 mmol) gave the crude product (6.4 g, 86%), which was purified by chromatography (0.5-3.5% MeOH/CH$_2$Cl$_2$). Yield 3.6 g (48%). TLC R$_f$(D) 0.39. $^1$H NMR (DMSO-d$_6$) δ 12.07 (s, 1H), 11.63 (s, 1H), 8.15 (s, 1H), 7.35-7.25 (m, 2H), 7.22-7.16 (m, 2H), 6.25 (t, J=7 Hz, 1H), 5.55 (d, J=4 Hz, 1H), 4.45 (m, 2H), 4.35 (m, 1H), 4.09 (m, 1H), 2.75 (m, 1H), 2.65 (m, 1H), 2.40 (s, 3H), 2.36 (m, 1H), 1.10 (m, 6H). $^{13}$C NMR δ 180.80, 155.51, 153.00, 149.10, 148.80, 147.97, 138.14, 131.96, 127.89, 127.41, 126.54, 122.68, 121.03, 84.55, 83.70, 71.03, 69.27, 39.54, 35.46, 19.53, 14.69. MS (−ESI, +Cl$^−$) calcd for C$_{22}$H$_{25}$ClN$_5$O$_7$S 538.1164 found 538.1176 (2.2 ppm).

5'-O-[2-(Methylthio)phenoxy]carbonyl-N$^4$-benzoyl-2'-deoxy cytidine (4c) Preparation with synthesis method 1 from 4$^6$-benzoyl-2'-deoxy cytidine (5 g, 15.1 mmol) gave the crude product (7.9 g, quantitative), which was purified by chromatography (0.5-3.5% MeOH/CH$_2$Cl$_2$). Yield 3.9 g (51%). TLC R$_f$(D) 0.55. $^1$H NMR (DMSO) δ 11.28 (bs, 1H), 8.09 (m, 1H), 7.99 (d, J=7 Hz, 1H), 7.60 (t, J=7 Hz, 1H), 7.49 (t, J=7 Hz, 2H), 7.37-7.18 (m, 5H), 6.17 (t, J=7 Hz, 1H), 5.54 (bs, 1H), 4.49-4.39 (m, 2H), 4.27 (m, 1H), 4.11 (m, 1H), 2.44 (s, 3H), 2.34-2.13 (m, 2H). $^{13}$C NMR δ 168.07, 163.81, 155.03, 152.91, 147.94, 145.37, 133.45, 131.94, 129.14, 127.94, 127.30, 126.55, 122.72, 87.15, 84.80, 70.74, 69.12, 14.62. MS (−ESI, +Cl⁻) calcd for $C_{25}H_{23}ClN_5O_6S$ 556.1058 found 556.1066 (1.4 ppm).

5'-O-[2-(Methylthio)phenoxy]carbonyl-3'-O-[(2-cyanoethyloxy)-N,N-(diisopropyl)amino-phosphityl]-N-6-benzoyl-2'-deoxy adenosine (5a) Using synthesis method 2b, compound (4a) (2.1 g, 4.0 mmol) in $CH_2Cl_2$ (50 ml), bisamidite reagent (2.0 ml, 4.2 mmol) and DCI (0.38 g, 3.2 mmol) gave the product that was purified on neutralized silica gel with 1:1:2 hexanes/$CH_2Cl_2$/EtOAc (1.7 g, 59%). TLC $R_f$(E) 0.25, 0.36 (diastereomer pair). $^{31}P$ NMR ($CD_3CN$) δ 149.69, 149.44. $^1H$ NMR ($CD_3CN$) δ 9.50 (bs, 1H), 8.65 (d, J=2 Hz, 1H), 8.31 (d, J=1 Hz, 1H), 7.98 (d, J=8 Hz, 2H), 7.61 (m, 1H), 7.52 (t, J=8 Hz, 2H), 7.32-7.24 (m, 2H), 7.18 (m, 1H), 7.07 (m, 1H), 6.49 (m, 1H), 4.91 (m, 1H), 4.52 (m, 2H), 4.39 (m, 1H), 3.84 (m, 2H), 3.68 (m, 2H), 2.98 (m, 1H), 2.75-2.59 (m, 1H), 2.70 (m, 2H), 2.39 (s, 3H), 1.19 (m, 12H). $^{13}C$ NMR δ 165.78, 153.00, 152.04, 150.19, 148.11, 142.78, 132.78, 131.92, 128.87, 128.38, 127.40, 127.28, 127.23, 127.19, 126.20, 125.05, 122.17, 118.88, 84.78, 83.83, 83.79, 83.62, 83.56, 73.54, 73.38, 73.27, 73.09, 68.19, 68.09, 58.92, 58.89, 58.74, 58.69, 43.43, 43.38, 43.30, 43.26, 38.47, 24.20, 24.15, 24.10, 20.36, 20.33, 20.29, 20.26, 14.32, 14.30. MS (−ESI, M−H⁺) calcd for $C_{34}H_{39}N_7O_7PS$ 720.237 found 720.2341 (4 ppm).

5'-O-[2-(Methylthio)phenoxy]carbonyl-3'-O-[(2-cyanoethyloxy)-N,N-(diisopropyl)amino-phosphityl]-N²-isobutyryl-2'-deoxy guanosine (5b) Using synthesis method 2b, compound (4b) (3.5 g, 6.9 mmol) in $CH_2Cl_2$ (50 ml), bisamidite reagent (3.5 ml, 7.3 mmol) and DCI (0.66 g, 5.6 mmol) gave the product that was purified on neutralized silica gel with 1:1:2 hexanes/$CH_2Cl_2$/EtOAc (3.7 g, 75%). TLC $R_f$(G) 0.63 (diastereomer pair). $^{31}P$ NMR ($CD_3CN$) δ 149.62, 149.34. $^1H$ NMR ($CD_3CN$) δ 7.86 (d, J=3 Hz, 1H), 7.67 (s, 1H), 7.34-7.27 (m, 2H), 7.20 (m, 1H), 7.11 (m, 1H), 6.26 (t, J=7 Hz, 1H), 4.75 (m, 1H), 4.54 (m, 2H), 4.37 (m, 1H), 3.83 (m, 2H), 3.65 (m, 2H), 2.87 (m, 1H), 2.70 (s, 2H), 2.76-2.59 (m, 1H), 2.40 (s, 3H), 1.20 (m, 12H). $^{13}C$ NMR δ 180.19, 180.16, 155.56, 153.24, 153.21, 148.61, 148.58, 148.25, 148.05, 138.26, 138.22, 131.93, 127.48, 127.10, 126.19, 122.20, 122.18, 121.79, 121.76, 118.96, 118.93, 84.92, 84.86, 83.81, 83.77, 83.67, 83.61, 74.11, 73.94, 73.79, 73.62, 68.49, 68.36, 58.70, 58.51, 58.43, 43.42, 43.37, 43.29, 43.25, 38.37, 38.33, 38.28, 35.89, 35.85, 24.18, 24.17, 24.15, 24.12, 20.36, 20.29, 19.88, 19.81, 18.48, 18.30, 14.28. MS (−ESI, +Cl⁻) calcd for $C_{31}H_{42}ClN_7O_8PS$ 738.2242 found 738.2218 (3.2 ppm).

5'-O-[2-(Methylthio)phenoxy]carbonyl-3'-O-[(2-cyanoethyloxy)-N,N-(diisopropyl)amino-phosphityl]-N⁴-benzoyl-2'-deoxy cytidine (5c) Using synthesis method 2b, compound (4c) (3.9 g, 7.8 mmol) in $CH_2Cl_2$ (100 ml), bisamidite reagent (3.96 ml, 8.22 mmol) and tetrazole in MeCN (17.4 ml, 7.8 mmol) gave the product that was purified on neutralized silica gel with 1:1:2 hexanes/$CH_2Cl_2$/EtOAc (2.9 g, 53%). TLC $R_f$ (E) 0.26, 0.45 (diastereomer pair). $^{31}P$ NMR ($CD_3CN$) δ 149.84, 149.51. $^1H$ NMR ($CD_3CN$) δ 9.24 (bs, 1H), 8.06 (d, J=7 Hz, 1H), 7.96 (d, J=7 Hz, 2H), 7.63 (t, J=7 Hz, 1H), 7.52 (t, J=7 Hz, 2H), 7.43 (m, 1H), 7.39-7.18 (m, 4H), 6.18 (m, 1H), 4.61-4.46 (m, 2H), 4.42 (m, 1H), 4.36 (m, 1H), 3.8 (m, 2H), 3.6 (m, 2H), 2.68 (t, J=7 Hz, 2H), 2.6 (m, 1H), 2.46 (s, 3H), 2.15 (m, 1H), 1.94 (m, 2H), 1.2 (m, 12H). $^{13}C$ NMR δ 162.99, 162.79, 154.81, 152.81, 148.08, 144.68, 133.10, 131.89, 128.85, 128.34, 127.50, 127.09, 126.26, 122.20, 122.18, 118.87, 96.57, 87.45, 84.12, 84.07, 83.90, 83.79, 83.75, 73.27, 73.19, 73.09, 73.02, 68.16, 68.01, 58.81, 58.64, 43.41, 43.38, 43.29, 43.26, 40.10, 24.18, 24.15, 24.11, 24.09, 20.29, 20.22, 14.28, 14.26. MS (−ESI, +Cl⁻) calcd for $C_{33}H_{40}ClN_5O_8PS$ 732.2024 found 732.2037 (1.8 ppm).

N⁶-anisoyl-2'-deoxy adenosine (6a) 2'-Deoxy adenosine (16 g, 59.4 mmol) was dissolved in abs. pyridine (300 ml) at 0° C. and anisoyl chloride (27 ml, 200 mmol) was added dropwise and stirred overnight. Water (3.6 ml) and acetone (100 ml) was added to the reaction mixture and precipitated into ice water (500 ml) and decantated. The crude product was dissolved in MeOH (800 ml) and NaOH solution (5 ml, 50%) was added and stirred for 90 min. The reaction mixture was filtered through pyridinium form Dowex 50Wx4 resin and evaporated. Chromatography (0-5% MeOH/$CH_2Cl_2$) resulted in the pure product (4.3 g, 19%). TLC $R_f$(D) 0.29. $^1H$ NMR (DMSO-$d_6$) δ 11.03 (bs, 1H), 8.72 (s, 1H), 8.66 (s, 1H), 8.02 (d, J=9 Hz, 2H), 7.06 (d, J=9 Hz, 2H), 6.47 (t, J=7 Hz, 1H), 5.37 (d, J=4 Hz, 1H), 5.03 (t, J=6 Hz, 1H), 4.44 (m, 1H), 3.89 (m, 1H), 3.84 (s, 3H), 3.65-3.50 (m, 2H), 2.79 (m, 1H), 2.35 (m, 1H). $^{13}C$ NMR δ 165.64, 163.26, 152.53, 152.23, 151.29, 143.58, 131.29, 126.47, 126.11, 114.38, 88.66, 84.39, 71.39, 62.29, 56.17. MS (−ESI, −H⁺) calcd for $C_{18}H_{18}ClN_5O_5$ 384.1308 found 384.1304 (1.0 ppm).

N⁴-(2,4,6-Trimethyl)benzoyl-2'-deoxy cytidine (6b) 2'-Deoxy cytidine hydrochloride (5 g, 18.9 mmol) was suspended in abs. pyridine (80 ml) and treated with trimethylsilyl chloride (12.2 ml, 96.5 mmol) and stirred for 15 min. 2,4,6-Trimethylbenzoyl chloride (10 g, 54.7 mmol) was then added to the reaction mixture and stirred overnight. The solvents were then evaporated off and the crude product was dissolved in acetone (200 ml), water (10 ml) and aq. cc. NH₄OH (310 ml) was added and stirred for 12 min at 0° C. Evaporation of the solvents and chromatography (0-5% MeOH/$CH_2Cl_2$) resulted in the product (3.4 g, 48%). TLC $R_f$(D) 0.24. $^1H$ NMR (DMSO) δ 11.14 (s, 1H), 8.39 (d, J=7 Hz, 1H), 7.35 (d, J=7 Hz, 1H), 6.87 (s, 2H), 6.09 (t, J=6 Hz, 1H), 5.27 (d, J=4 Hz, 1H), 5.07 (t, J=5 Hz, 1H), 4.22 (m, 1H), 3.86 (m, 1H), 3.65-3.54 (m, 2H), 2.33-2.27 (m, 1H), 2.23 (s, 3H), 2.18 (s, 6H), 2.04 (m, 1H). $^{13}C$ NMR δ 171.31, 162.99, 155.15, 145.90, 138.81, 135.14, 134.17, 128.59, 96.37, 88.64, 86.99, 70.56, 61.59, 41.57, 21.38, 19.53. MS (−ESI, +Cl⁻) calcd for $C_{19}H_{23}ClN_3O_5$ 408.1327 found 408.1333 (1.5 ppm).

5'-O-[2-(Methylthio)phenoxy]carbonyl-N-6-anisoyl-2'-deoxy adenosine (7a) From 20% phosgene solution in toluene (22.5 ml, 45 mmol), 2-methylthio phenol (1.26 g, 9 mmol) and TEA (1.38 ml, 9.9 mmol) at 0° C. the chloroformate was made using synthesis method 1. N⁶-Anisoyl-2'-deoxy adenosine (6a) (2.85 g, 7.39 mmol) was dried by evaporation off abs. pyridine (3×30 ml) and dissolved in the same solvent (50 ml) and cooled to −78° C. The above chloroformate, dissolved in abs. $CH_2Cl_2$ (22.5 ml) was added to the frozen solution of protected adenosine and shaken until everything dissolved. The reaction mixture was stirred overnight, pyridine was evaporated off and the crude product was purified by chromatography (0-3% MeOH/$CH_2Cl_2$) to give the product (1.2 g, 29%). TLC $R_f$(D) 0.45. $^1H$ NMR (DMSO-$d_6$) δ 11.05 (s, 1H), 8.73 (s, 1H), 8.62 (s, 1H), 8.03 (d, J=8 Hz, 2H), 7.38-7.14 (m, 4H), 7.06 (d, J=8 Hz, 2H), 6.53 (t, J=6 Hz, 1H), 5.62 (d, J=4 Hz, 1H), 4.57 (m, 1H), 4.53-4.38 (m, 2H), 4.14 (m, 1H), 3.84 (s, 3H), 2.88 (m, 1H), 2.43-2.29 (m, 1H), 2.38 (s, 3H). $^{13}C$ NMR δ 165.63, 163.26, 153.03, 152.50, 152.34, 151.37, 148.00, 143.61, 131.99, 131.30, 127.85, 127.40, 126.54, 126.49, 126.12, 122.72, 114.39, 84.66, 84.36, 71.17, 69.24, 56.18, 39.12, 14.68. MS (−ESI, +Cl⁻) calcd for $C_{26}H_{25}ClN_5O_7S$ 586.1164 found 586.1163 (0.2 ppm).

5'-O-[2-(Methylthio)phenoxy]carbonyl-N⁴-(2,4,6-trimethyl)benzoyl-2'-deoxy cytidine (7b) From 20% phosgene solution in toluene (27.5 ml, 55 mmol), 2-methylthio phenol (1.54 g, 11 mmol) and TEA (1.68 ml, 12.1 mmol) at 0° C. the chloroformate was made using synthesis method 1. N-(2,4,6-Trimethyl)benzoyl-2'-deoxy cytidine (6b) (3.35 g, 8.97 mmol) was dried by evaporation off abs. pyridine (3×30 ml) and dissolved in the same solvent (50 ml) and cooled to −78° C. The above chloroformate, dissolved in abs. $CH_2Cl_2$ (27.5 ml) was added to the frozen solution of protected cytosine and shaken until everything dissolved. The reaction mixture was stirred overnight, pyridine was evaporated off and the crude product was purified by chromatography (0-3% MeOH/$CH_2Cl_2$) to give the product (3.2 g, 66%). TLC $R_f$(D) 0.5. $^1$H NMR ($CD_3CN$) δ 9.23 (bs, 1H), 8.14 (d, J=6 Hz, 2H), 7.51 (m, 2H), 7.38 (d, J=5 Hz, 1H), 7.33 (t, J=5 Hz, 1H), 7.24 (m, 2H), 6.92 (s, 1H), 6.15 (t, J=5 Hz, 1H), 4.55 (m, 1H), 4.46 (m, 1H), 4.40 (m, 1H), 4.24 (m, 1H), 3.72 (m, 1H), 2.49 (s, 3H), 2.5-2.46 (m, 1H), 2.30 (s, 3H), 2.27 (s, 6H), 2.10-2.05 (m, 1H). $^{13}$C NMR δ 170.85, 162.56, 154.99, 152.94, 148.08, 144.94, 139.50, 134.29, 131.90, 128.28, 127.48, 127.09, 126.23, 122.21, 96.07, 87.35, 84.72, 70.68, 68.32, 40.94, 20.45, 18.57, 14.23. MS (−ESI, +Cl⁻) calcd for $C_{27}H_{29}ClN_3O_7S$ 574.1415 found 574.1435 (3.5 ppm).

5'-O-[2-(Methylthio)phenoxy]carbonyl-3'-O-[(2-cyanoethyloxy)-N,N-(diisopropyl)amino-phosphityl]-N-6-anisoyl-2'-deoxy adenosine (8a) Using synthesis method 2b, compound (7a) (1.2 g, 2.18 mmol) in $CH_2Cl_2$ (50 ml), bisamidite reagent (1.05 ml, 2.18 mmol) and tetrazole solution in abs. MeCN (0.45 M, 3.9 ml, 1.74 mmol) gave the product that was chromatographed on neutralized silica gel with 1:1:2 hexanes/$CH_2Cl_2$/EtOAc (1.04 g, 63%). TLC $R_f$ (E) 0.20, 0.30 (diastereomer pair). $^{31}$P NMR ($CD_3CN$) δ 149.64, 149.37. $^1$H NMR δ 9.81 (bs, 1H), 8.60 (m, 1H), 8.30 (s, 1H), 7.93 (d, J=8 Hz, 2H), 7.28-7.21 (m, 2H), 7.18-7.13 (m, 1H), 7.09-7.05 (m, 1H), 6.92 (d, J=8 Hz, 2H), 6.47 (m, 1H), 4.89 (m, 1H), 4.60-4.44 (m, 2H), 4.41-4.36 (m, 1H), 3.91-3.75 (m, 2H), 3.81 (s, 3H), 3.65 (m, 2H), 2.99-3.93 (m, 1H), 2.69 (m, 2H), 2.64-2.53 (m, 1H), 2.37 (s, 3H), 1.21 (m, 12H). $^{13}$C NMR δ 165.31, 163.25, 153.00, 151.99, 151.87, 150.53, 148.10, 142.66, 131.92, 130.56, 127.41, 127.19, 127.13, 126.20, 124.95, 122.17, 118.93, 113.91, 84.74, 83.84; 83.80, 83.62, 83.56, 73.61, 73.45, 73.35, 73.17, 68.28, 68.18, 58.94, 58.76, 58.51, 58.46, 55.57, 43.44, 43.40, 43.32, 43.28, 38.53, 38.49, 24.30, 24.26, 24.19, 20.42, 20.38, 20.35, 20.31, 14.41, 14.38. MS (−ESI, +Cl⁻) calcd for $C_{35}H_{42}ClN_7O_8PS$ 786.2242 found 786.2234 (1.0 ppm).

5'-O-[2-(Methylthio)phenoxy]carbonyl-3'-O-[(2-cyanoethyloxy)-N,N-(diisopropyl)amino-phosphityl]-$N^4$-(2,4,6-Trimethyl)benzoyl-2'-deoxy cytidine (8b) Using synthesis method 2b, compound (7b) (3.2 g, 5.93 mmol) in $CH_2Cl_2$ (100 ml), bisamidite reagent (2.80 ml, 5.93 mmol) and tetrazole solution in abs. MeCN (0.45 M, 10.54 ml, 4.74 mmol) gave the product that was chromatographed on neutralized silica gel with 1:1:2 hexanes/$CH_2Cl_2$/EtOAc (3.7 g, 84%). TLC $R_f$ (F) 0.58, 0.68 (diastereomer pair). $^{31}$P NMR ($CD_3CN$) δ 149.83, 149.49. $^1$H NMR δ 9.60 (bs, 1H), 8.08 (d, J=7 Hz, 2H), 7.51 (d, J=7 Hz, 2H), 7.36-7.27 (m, 2H), 7.24-7.17 (m, 2H), 6.84 (s, 2H), 6.04 (m, 1H), 4.58 (m, 1H), 4.49 (m, 2H), 4.43-4.37 (m, 1H), 3.87-3.74 (m, 2H), 3.69-3.58 (m, 2H), 2.68 (m, 2H), 2.63-2.50 (m, 1H), 2.46 (s, 3H), 2.28 (s, 3H), 2.22 (s, 6H), 2.15-2.05 (m, 1H), 1.20 (m, 12H). $^{13}$C NMR δ 170.95, 162.69, 154.68, 152.81, 148.08, 144.99, 139.36, 134.26, 134.21, 131.91, 128.27, 127.53, 127.13, 127.06, 126.26, 122.22, 122.20, 118.88, 118.84, 96.20, 87.48, 87.43, 84.22, 84.18, 83.91, 83.85, 73.39, 73.35, 73.22, 73.17, 68.20, 68.05, 58.87, 58.81, 58.68, 58.62, 43.44, 43.41, 43.32, 43.29, 40.29, 40.26, 24.23, 24.16, 20.61, 20.33, 20.26, 18.72, 14.32, 14.29. MS (−ESI, +Cl⁻) calcd for $C_{36}H_{46}ClN_5O_8PS$ 774.2494 MS 774.2490 (0.5 ppm).

What is claimed is:

1. A compound having one of the following structures:

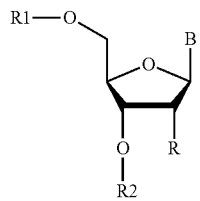 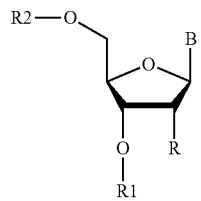 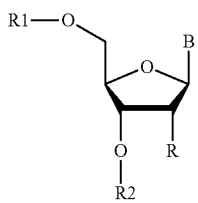 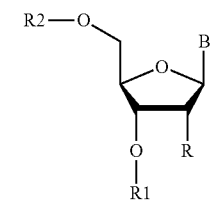

wherein:

B is a heterocyclic base;

R is hydrido, hydroxyl or a protected hydroxyl group;

R1 is a thioether substituted aryl carbonate protecting group, said protecting group having an aryl ring and a thioether substituent bound directly to the aryl ring; and R2 is a phosphoramidite.

2. The compound according to claim 1, wherein R1 has the structure:

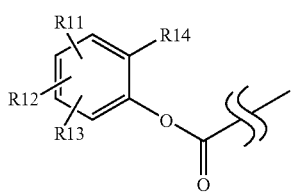

wherein:

R11 is a thioether moiety R15-S~;

R12 and R13 are each independently a hydrido, a thioether moiety or an electron-withdrawing substituent; and R14 is a hydrido, a thioether moiety R18-S~, an electron-withdrawing substituent or ~O—C(O)—R19;

wherein the tilde (~) denotes the bond to a ring carbon of structure (III) and R15, R18 and R19 are each independently selected from lower alkyl, substituted lower alkyl, alkyl, substituted alkyl, and aryl.

3. A method comprising:

(a) contacting a first nucleoside moiety comprising a free hydroxyl group with a compound having one of the following structures:

wherein:

B is a heterocyclic base;

R is hydrido or a protected hydroxyl group;

R1 is a thioether substituted aryl carbonate protecting group, said protecting group having an aryl ring and a thioether substituent bound directly to the aryl ring; and R2 is a phosphoramidite;

under conditions sufficient to produce a product in which said first nucleoside moiety is covalently bonded to said compound via a phosphite linkage; and (b) exposing said product to an oxidizing and deprotecting reagent comprising a nucleophile that exhibits an alpha effect at neutral to mildly basic pH to oxidize said phosphite linkage and remove said thioether substituted aryl carbonate protecting group; and (c) repeating steps (a) and (b) as necessary to synthesize a polynucleotide having a desired sequence and length.

4. The method according to claim 3, wherein said first nucleoside moiety is covalently bonded to a solid support.

5. The method according to claim 3, wherein R1 has the structure:

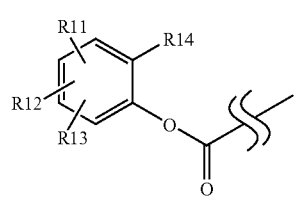

wherein:

R11 is a thioether moiety R15-S~;

R12 and R13 are each independently a hydrido, a thioether moiety or an electron-withdrawing substituent; and R14 is a hydrido, a thioether moiety R18-S~, an electron-withdrawing substituent or ~O—C(O)—R19;

wherein the tilde (~) denotes the bond to a ring carbon of structure (III) and R15, R18 and R19 are each independently selected from lower alkyl, substituted lower alkyl, alkyl, substituted alkyl, and aryl.

6. The method according to claim 3, wherein said polynucleotide is bonded to a solid support.

7. The method according to claim 6, wherein said method further comprises separating said polynucleotide from said solid support to produce a free polynucleotide.

8. The method according to claim 7, wherein said method further comprises combining said free polynucleotide with a pharmaceutically acceptable carrier to form a pharmaceutically acceptable composition.

9. The method according to claim 7, wherein said method further comprises chemically modifying said free polynucleotide to produce a modified free polynucleotide.

10. The method according to claim 9, wherein said method further comprises combining said modified free polynucleotide with a pharmaceutically acceptable composition.

11. The method according to claim 3, wherein said polynucleotide is a DNA.

12. The method according to claim 3, wherein said polynucleotide is a RNA.

* * * * *

UNITED STATES PATENT AND TRADEMARK OFFICE
CERTIFICATE OF CORRECTION

| | | |
|---|---|---|
| PATENT NO. | : 8,097,711 B2 | Page 1 of 1 |
| APPLICATION NO. | : 11/897898 | |
| DATED | : January 17, 2012 | |
| INVENTOR(S) | : Zoltan Timar et al. | |

It is certified that error appears in the above-identified patent and that said Letters Patent is hereby corrected as shown below:

On the face page, in field (57), under "Abstract", in column 2, line 10, delete "monomer monomers," and insert -- monomer/monomers, --, therefor.

Signed and Sealed this
Twenty-eighth Day of February, 2012

David J. Kappos
*Director of the United States Patent and Trademark Office*